US012734390B2

(12) United States Patent
Choi

(10) Patent No.: US 12,734,390 B2
(45) Date of Patent: Sep. 15, 2026

(54) REHABILITATION EXERCISE DEVICE FOR UPPER AND LOWER LIMBS

(71) Applicant: H ROBOTICS INC., Pohang-si (KR)

(72) Inventor: Dong-Min Choi, Suwon-si (KR)

(73) Assignee: H ROBOTICS INC., Pohang-si (KR)

( * ) Notice: Subject to any disclaimer, the term of this patent is extended or adjusted under 35 U.S.C. 154(b) by 1150 days.

(21) Appl. No.: 17/779,529

(22) PCT Filed: Jan. 13, 2021

(86) PCT No.: PCT/KR2021/000439
§ 371 (c)(1),
(2) Date: May 24, 2022

(87) PCT Pub. No.: WO2021/172745
PCT Pub. Date: Sep. 2, 2021

(65) Prior Publication Data

US 2022/0401783 A1 Dec. 22, 2022

(30) Foreign Application Priority Data

Feb. 25, 2020 (KR) ........................ 10-2020-0022972
Oct. 29, 2020 (KR) ........................ 10-2020-0141794
Jan. 12, 2021 (KR) ........................ 10-2021-0004009

(51) Int. Cl.
*A63B 21/00* (2006.01)
*A63B 21/005* (2006.01)
(Continued)

(52) U.S. Cl.
CPC .. *A63B 21/00181* (2013.01); *A63B 21/00178* (2013.01); *A63B 21/0058* (2013.01);
(Continued)

(58) Field of Classification Search
CPC ............ A63N 21/00181; A61H 1/0237; A61H 1/024; A61H 1/0244; A61H 1/0266;
(Continued)

(56) References Cited

U.S. PATENT DOCUMENTS

2022/0110816 A1* 4/2022 Aoki .................... A61F 5/0125

FOREIGN PATENT DOCUMENTS

JP 2018075262 A * 5/2018

OTHER PUBLICATIONS

Machine translation of JP-2018075262-A. Accessed from PE2E search tool (Jan. 2026) (Year: 2018).*

* cited by examiner

*Primary Examiner* — Joseph D. Boecker
*Assistant Examiner* — Jaeick Jang
(74) *Attorney, Agent, or Firm* — Quantum Patent Law Firm; Seongyoune Kang

(57) ABSTRACT

The present invention relates to a rehabilitation exercise system for upper and lower limbs, comprising: a rehabilitation exercise device for rehabilitation of arms or legs and an information processing terminal which is connected to the rehabilitation exercise device via a wireless communication network; wherein the rehabilitation exercise device comprises at least one type of sensors which detect a first information; wherein the information processing terminal is configured to transmit a second information to the rehabilitation exercise device via the wireless communication network; wherein the rehabilitation exercise device is configured to control a rehabilitation exercise load based on the first information and the second information. Therefore, it is possible to provide a more efficient rehabilitation by controlling a rehabilitation exercise load of the rehabilitation exercise device based on the first information detected by
(Continued)

the rehabilitation exercise device and the second information received from the information processing terminal.

8 Claims, 29 Drawing Sheets

(51) Int. Cl.

| | |
|---|---|
| ***A63B 23/035*** | (2006.01) |
| ***A63B 23/04*** | (2006.01) |
| ***A63B 23/12*** | (2006.01) |
| ***A63B 24/00*** | (2006.01) |
| ***G06K 19/07*** | (2006.01) |
| ***G16H 20/30*** | (2018.01) |
| ***H04M 1/72409*** | (2021.01) |

(52) U.S. Cl.

CPC .... *A63B 21/4047* (2015.10); *A63B 23/03508* (2013.01); *A63B 23/04* (2013.01); *A63B 23/12* (2013.01); *A63B 24/0062* (2013.01); *G06K 19/0723* (2013.01); *G16H 20/30* (2018.01); *A63B 2024/0093* (2013.01); *A63B 2220/16* (2013.01); *A63B 2220/89* (2013.01); *A63B 2225/50* (2013.01); *H04M 1/72409* (2021.01)

(58) Field of Classification Search

CPC .. A61H 1/0277; A61H 1/0274; A61H 1/0281; A61H 1/0285; A61H 2201/12; A61H 2201/50; A61H 2201/5007; A61H 2201/501; A61H 2201/5012; A61H 2201/5058

See application file for complete search history.

[FIG. 1]
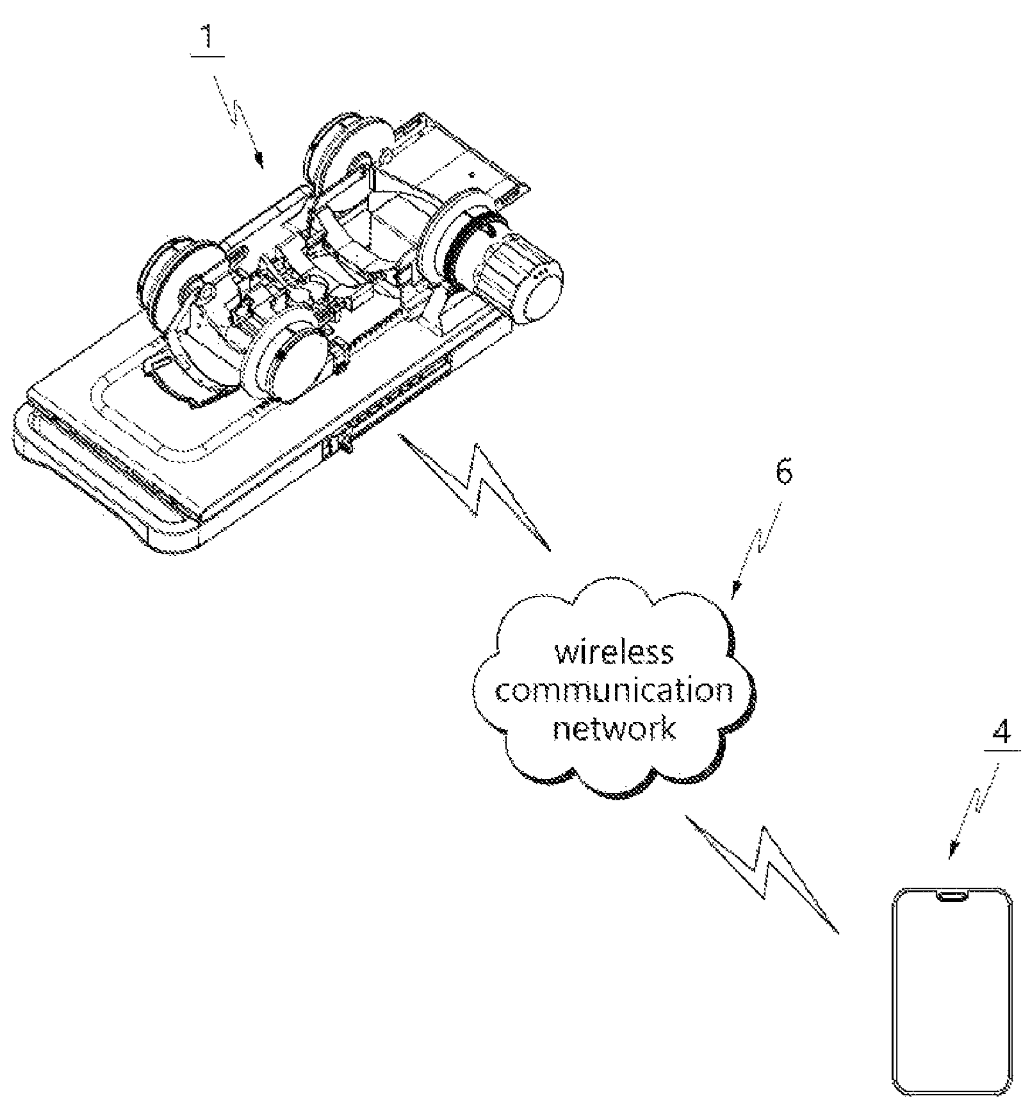

[FIG. 2]
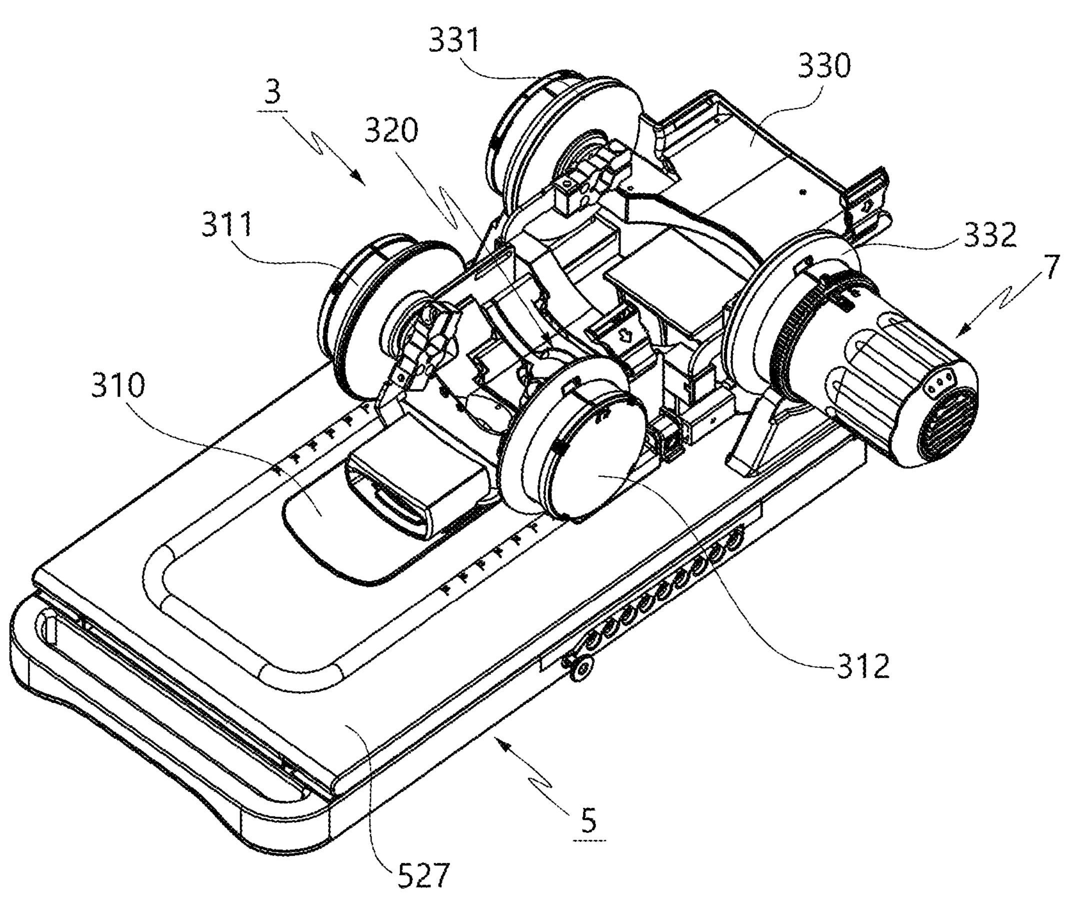

[FIG. 3]
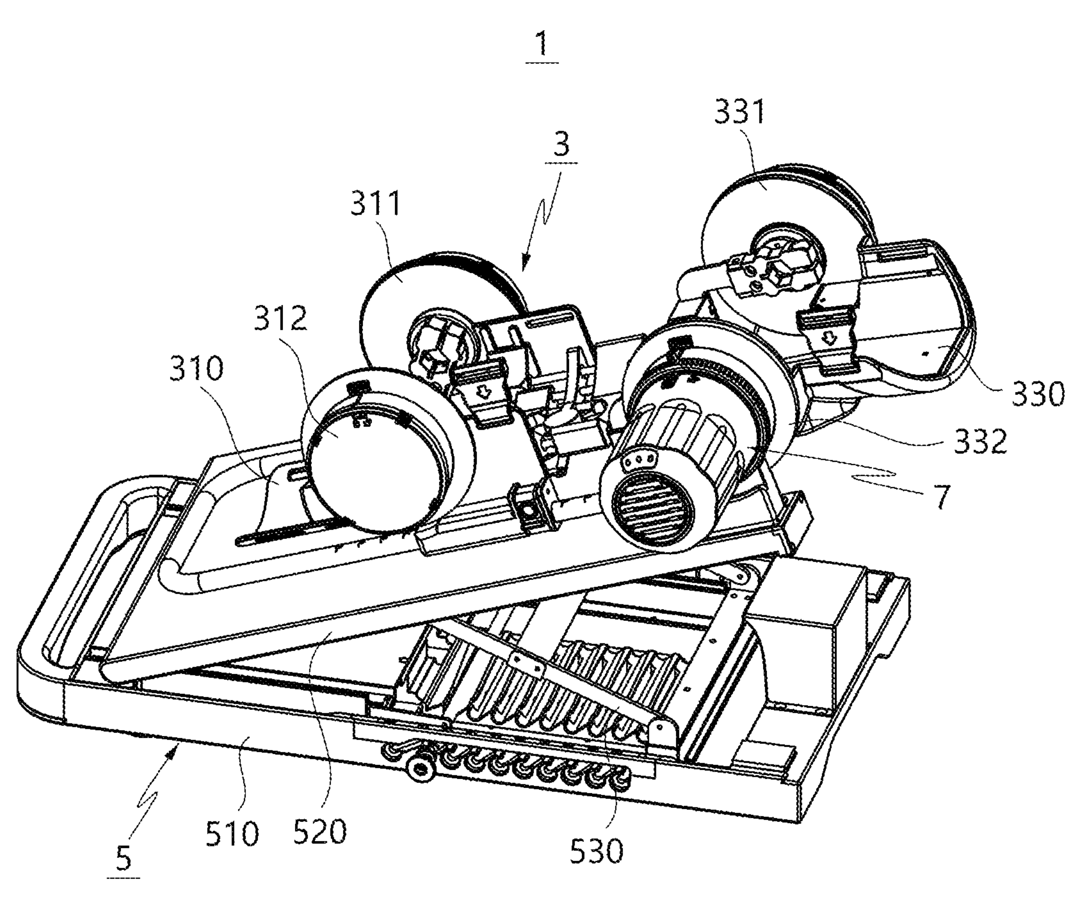

[FIG. 4]
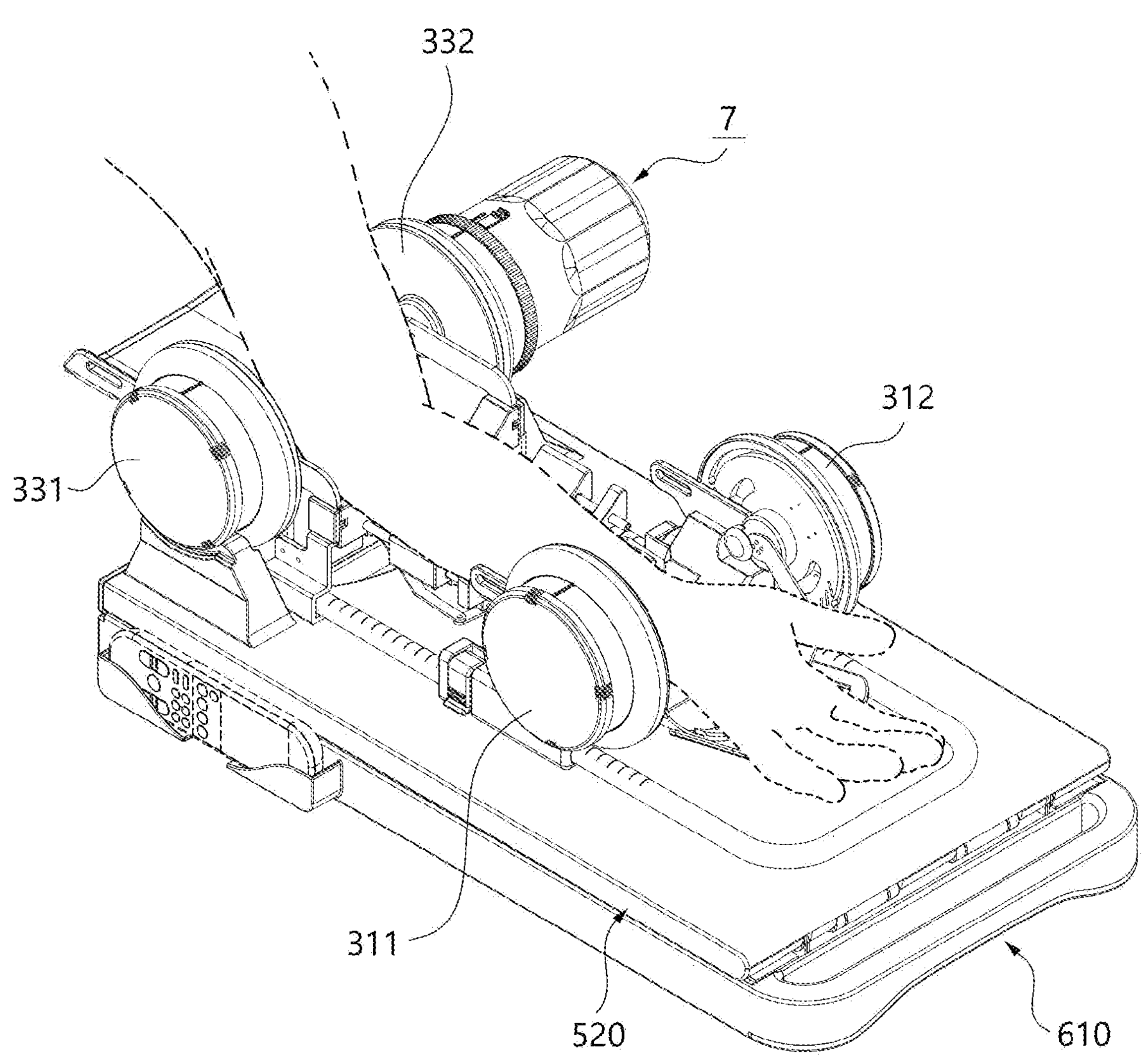

[FIG. 5]
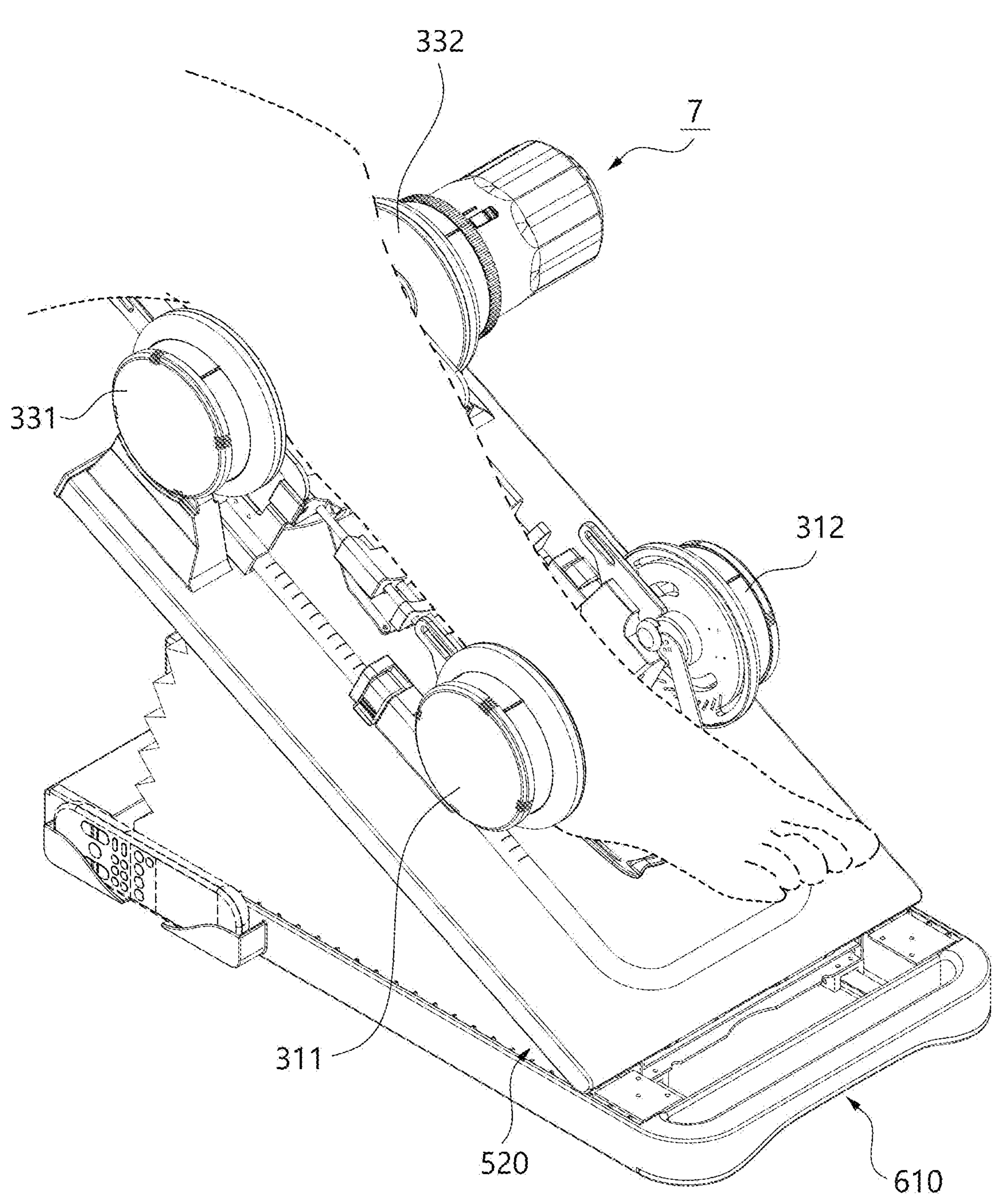

[FIG. 6]
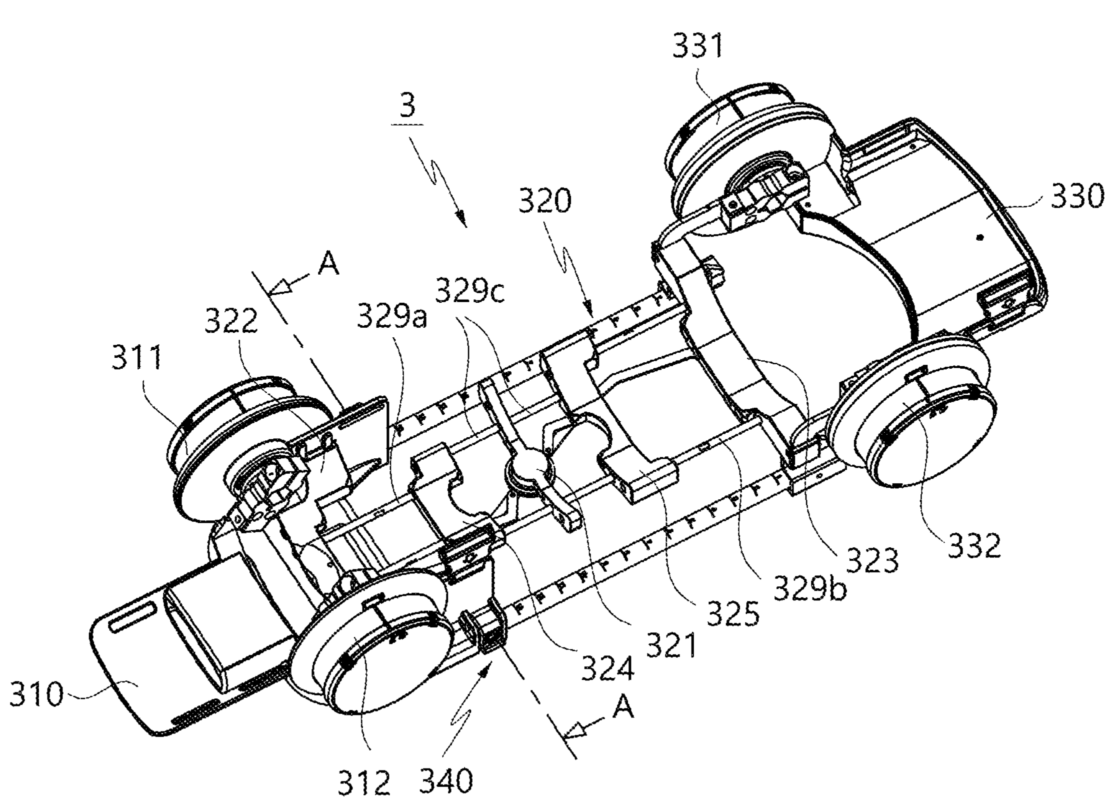

[FIG. 7]
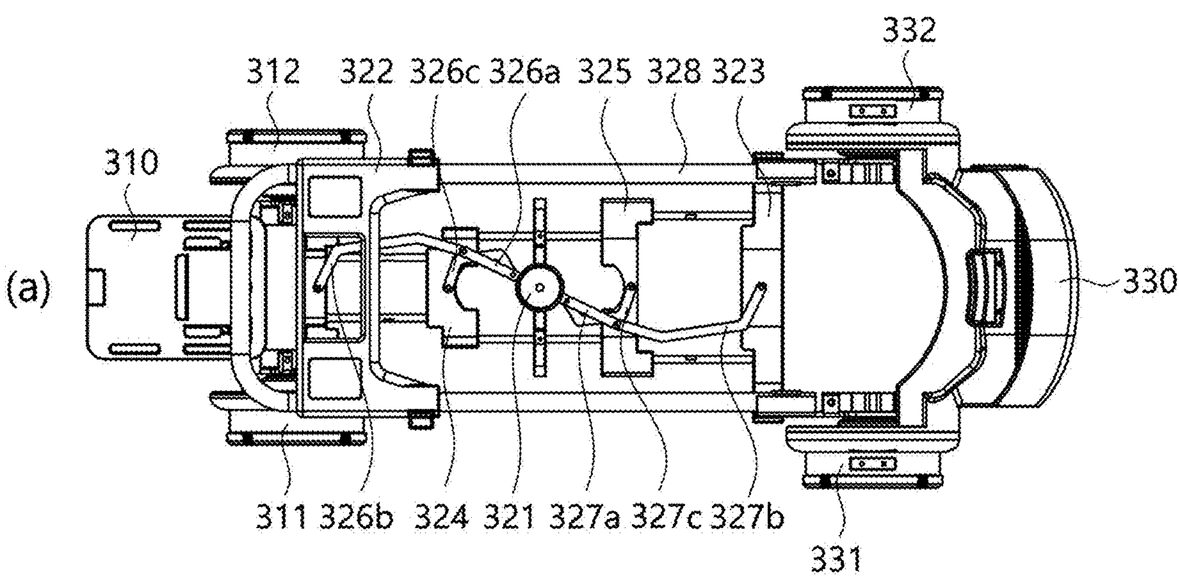
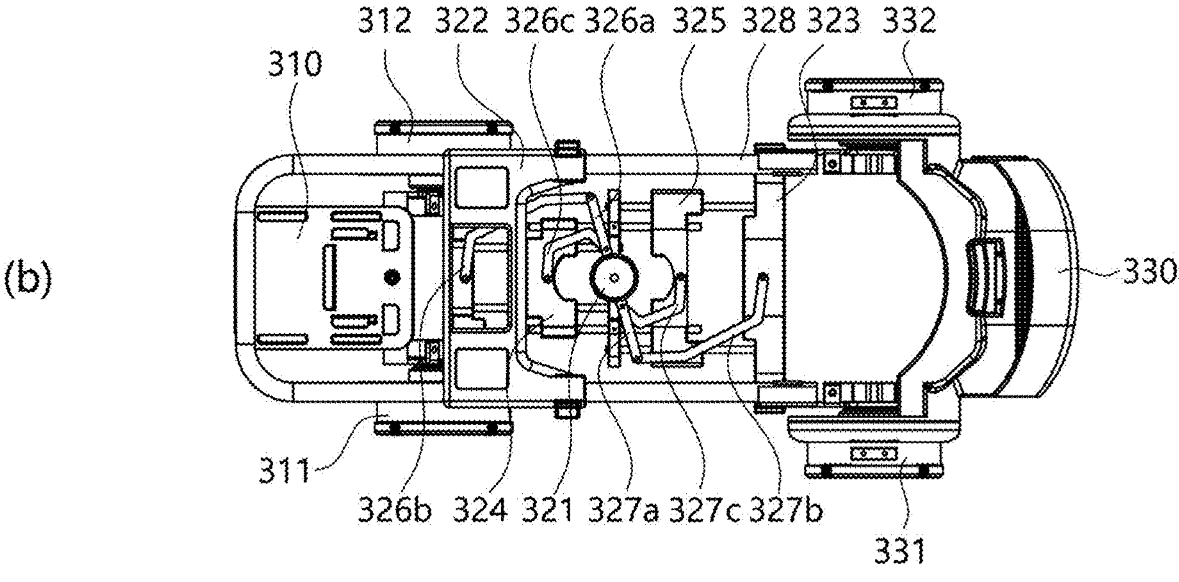

[FIG. 8]
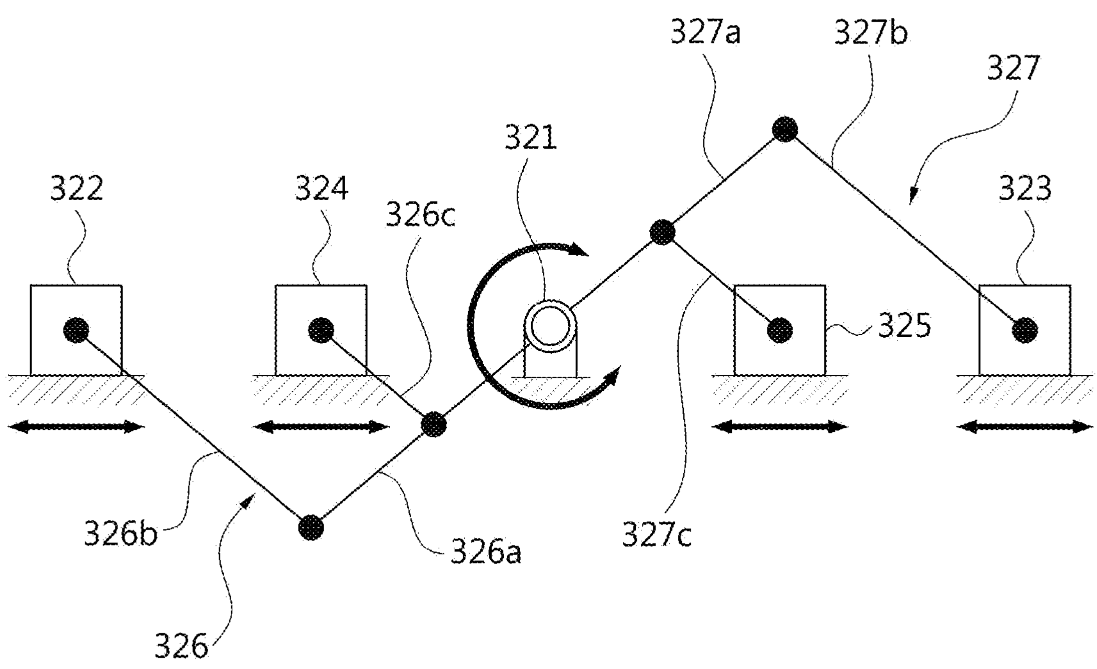
[FIG. 9]
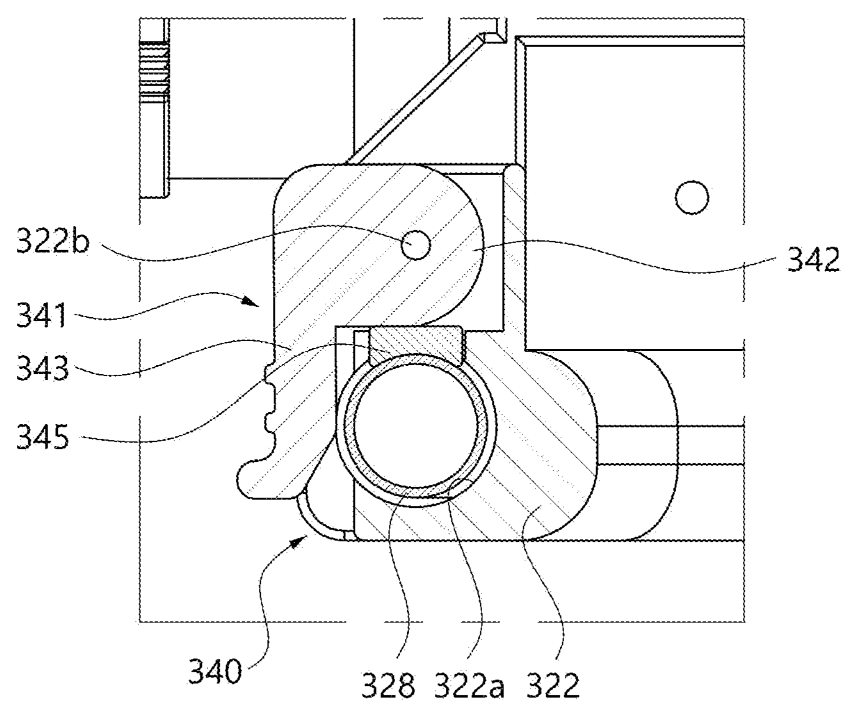

[FIG. 10]
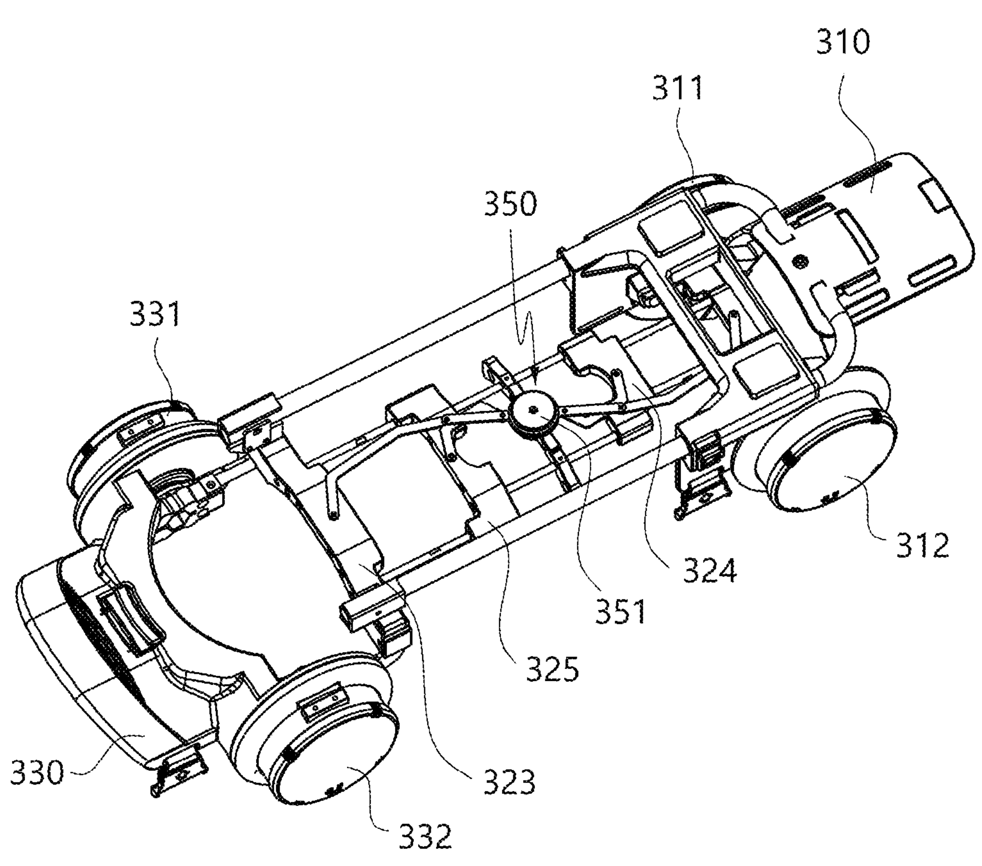

[FIG. 11]
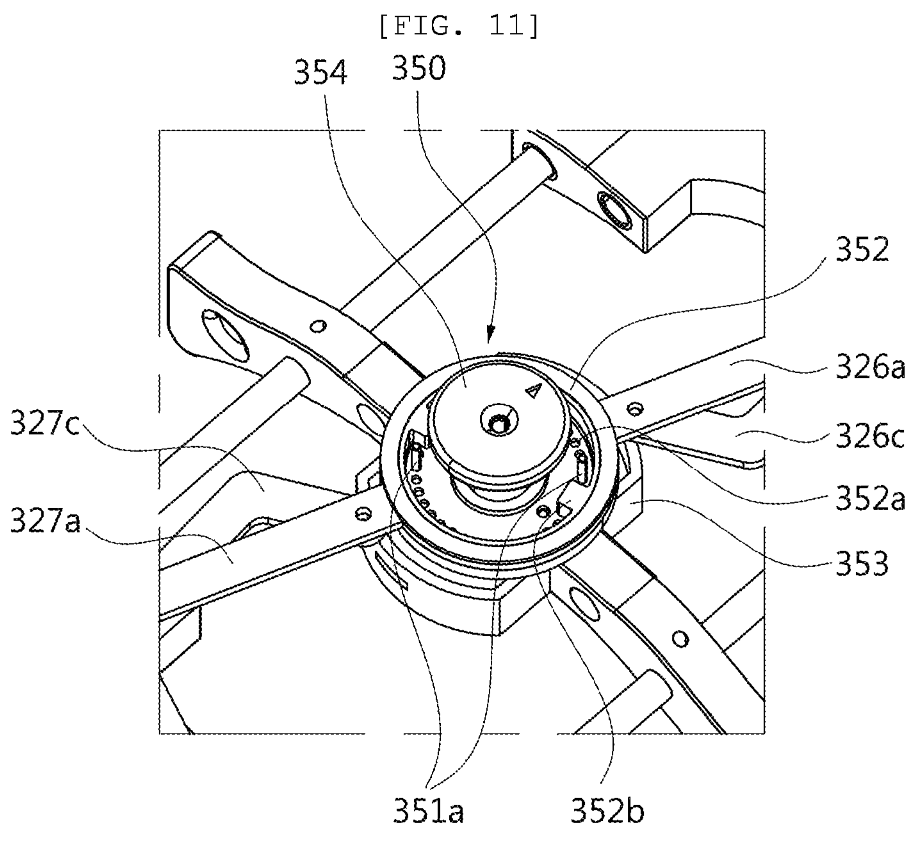
[FIG. 12]
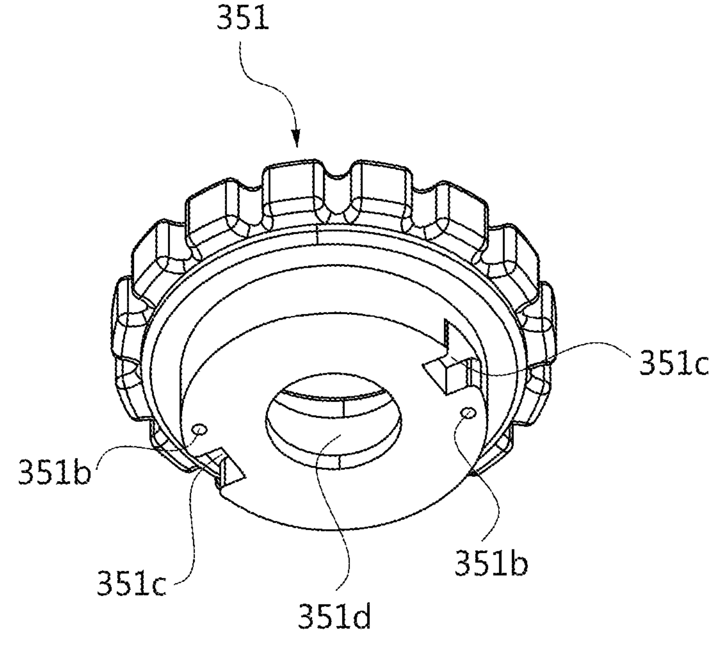

[FIG. 13]
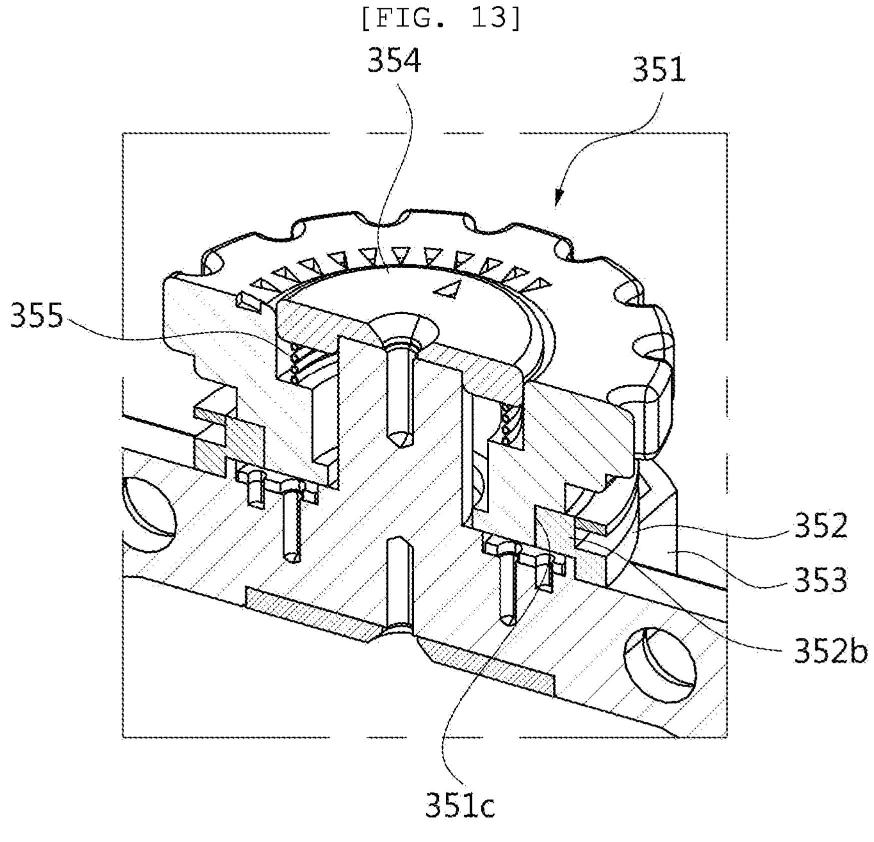
[FIG. 14]
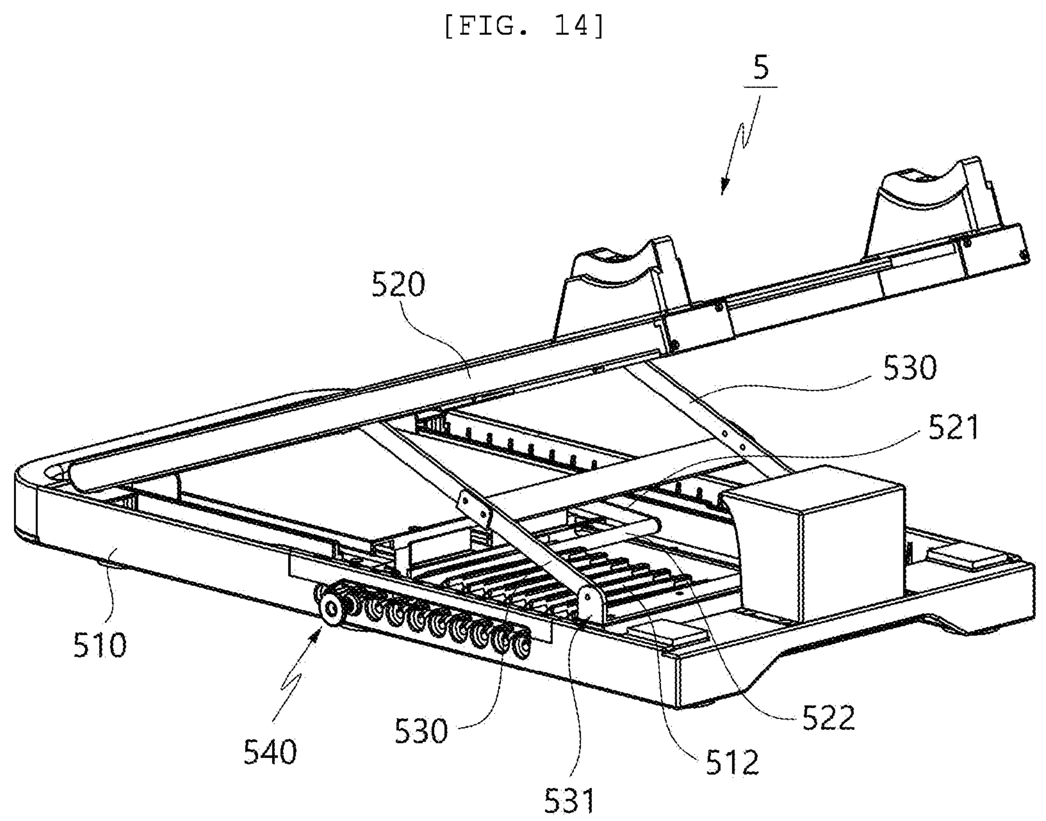

[FIG. 15]
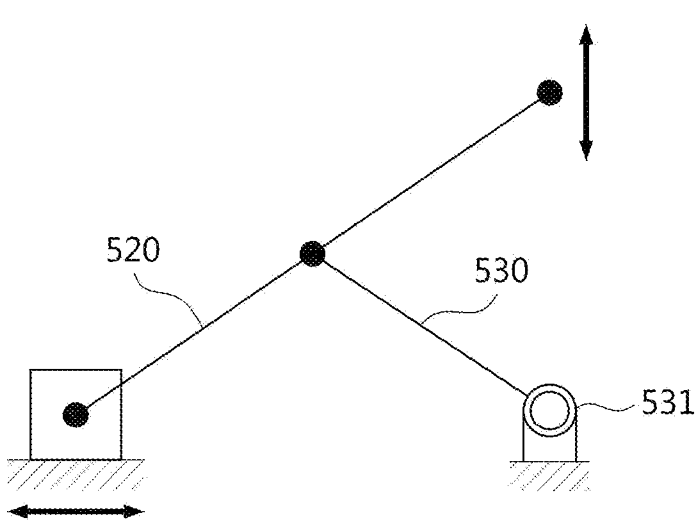

[FIG. 16]
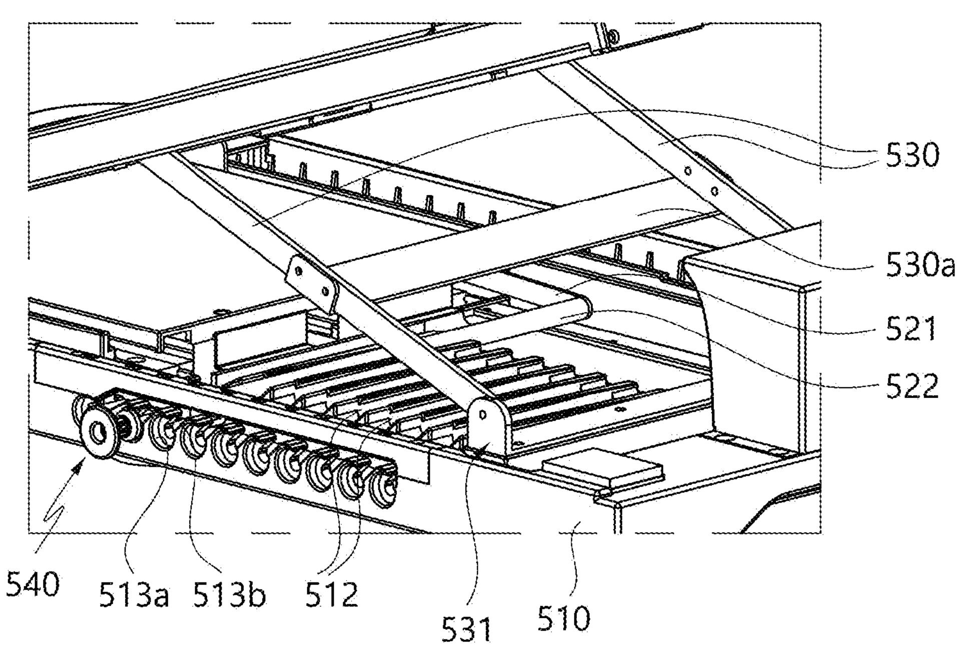

[FIG. 17]
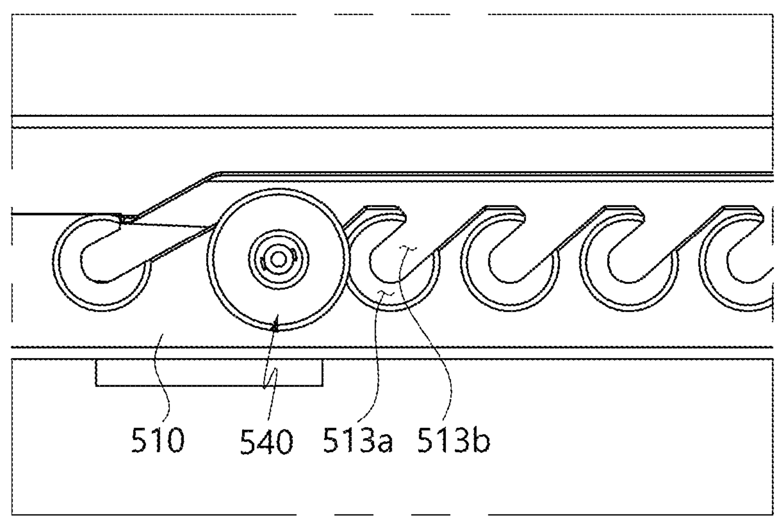

[FIG. 18]
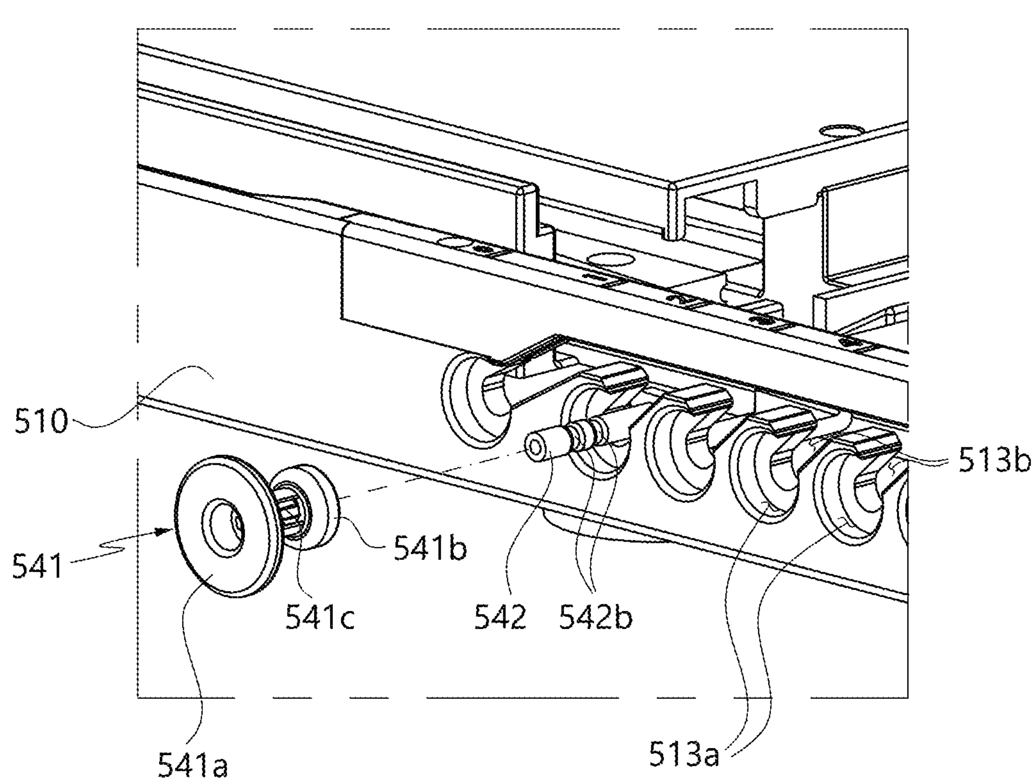

[FIG. 19]
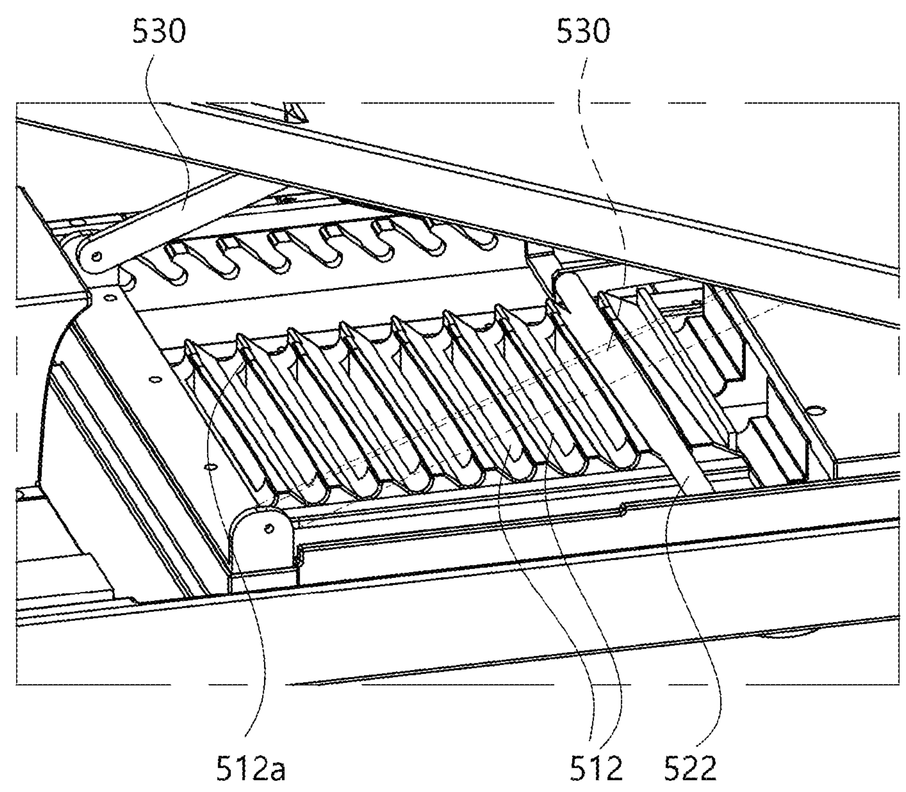

[FIG. 20]
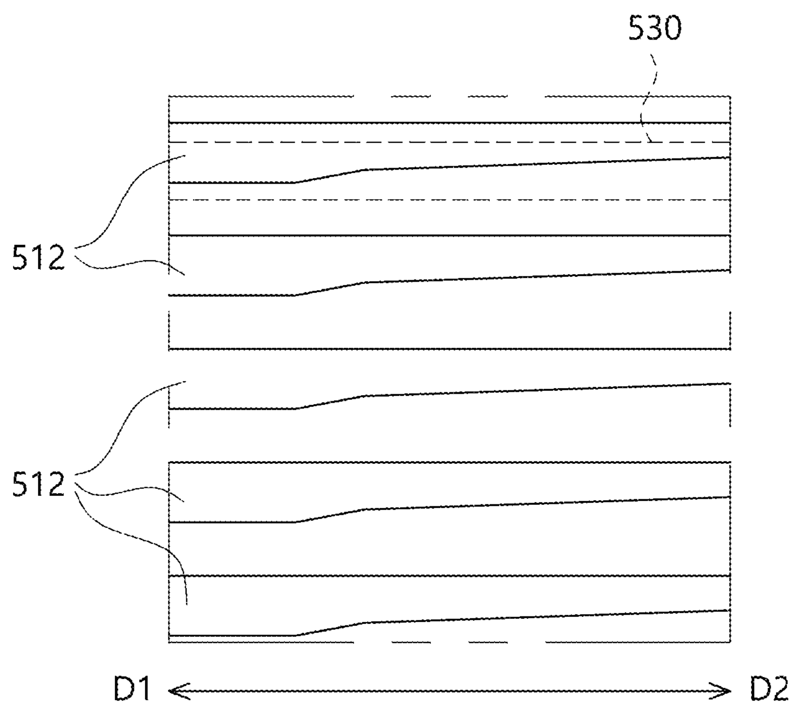

[FIG. 21]
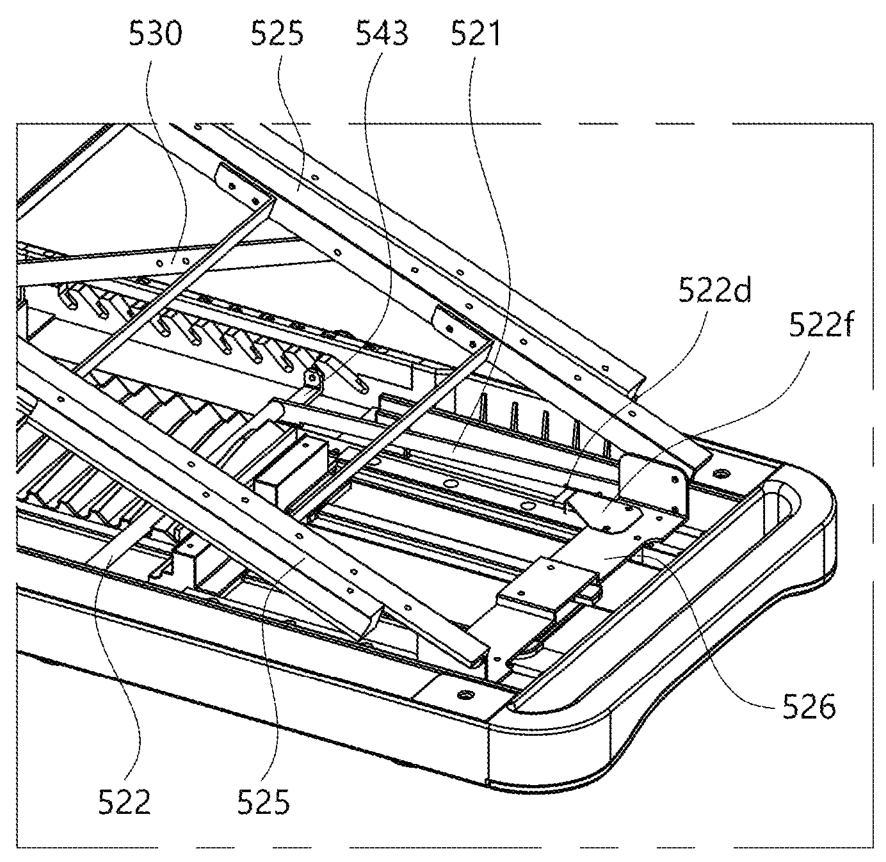

[FIG. 22]
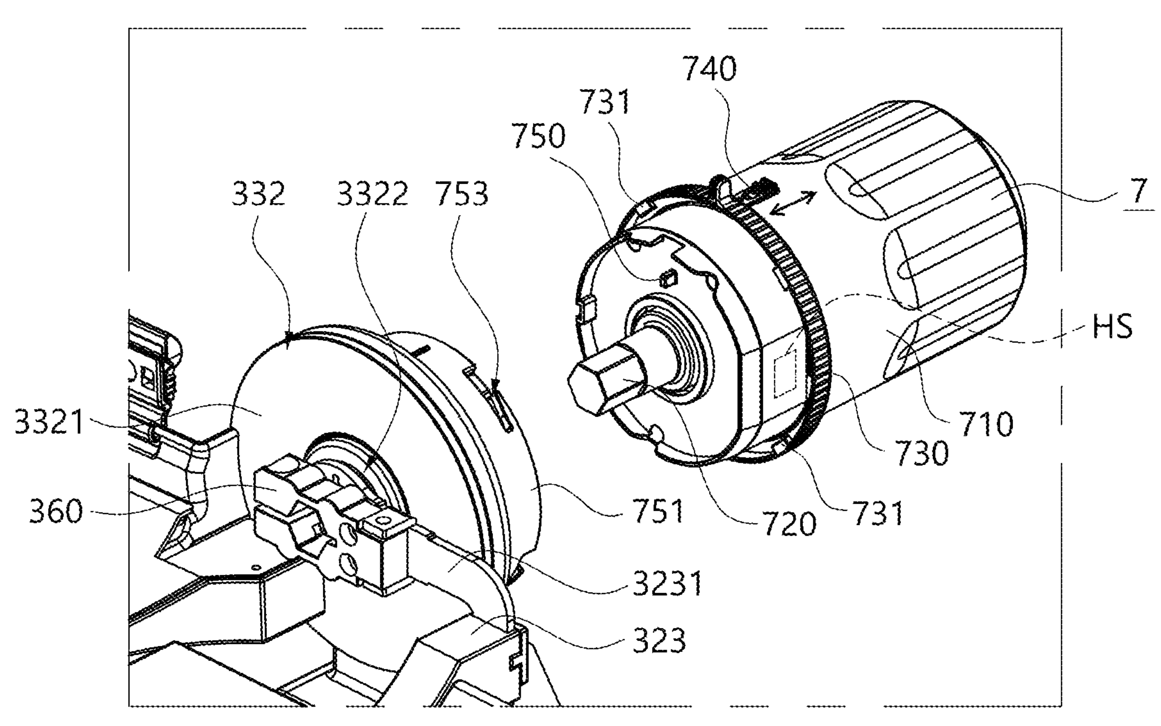

[FIG. 23]
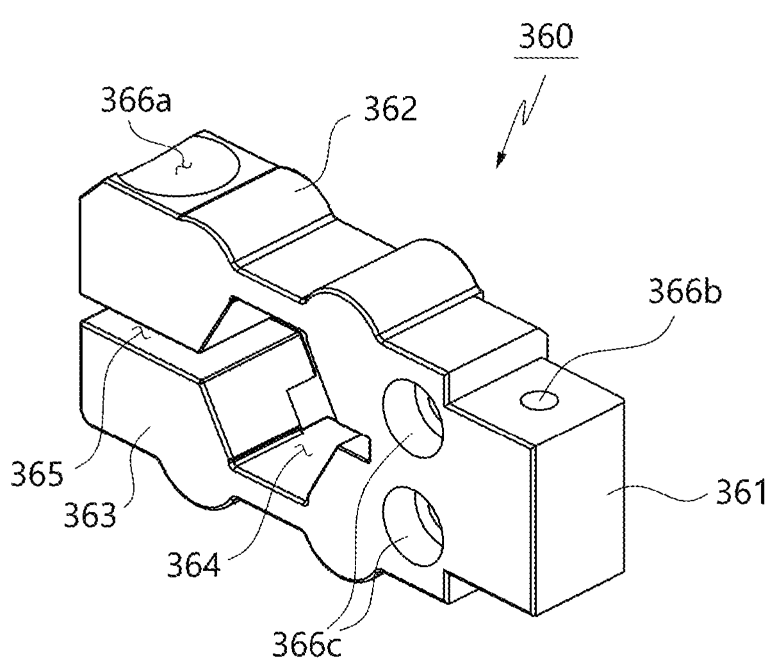

[FIG. 24]
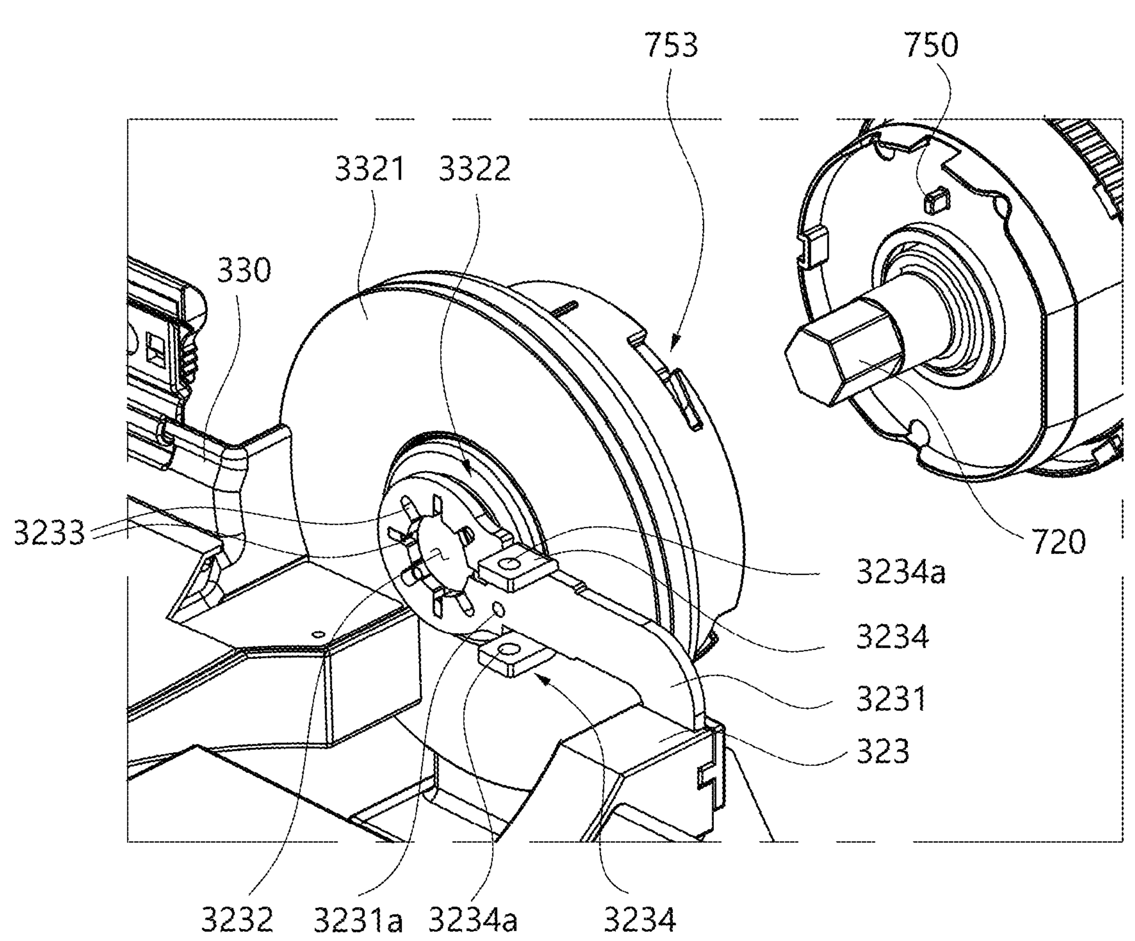

[FIG. 25]
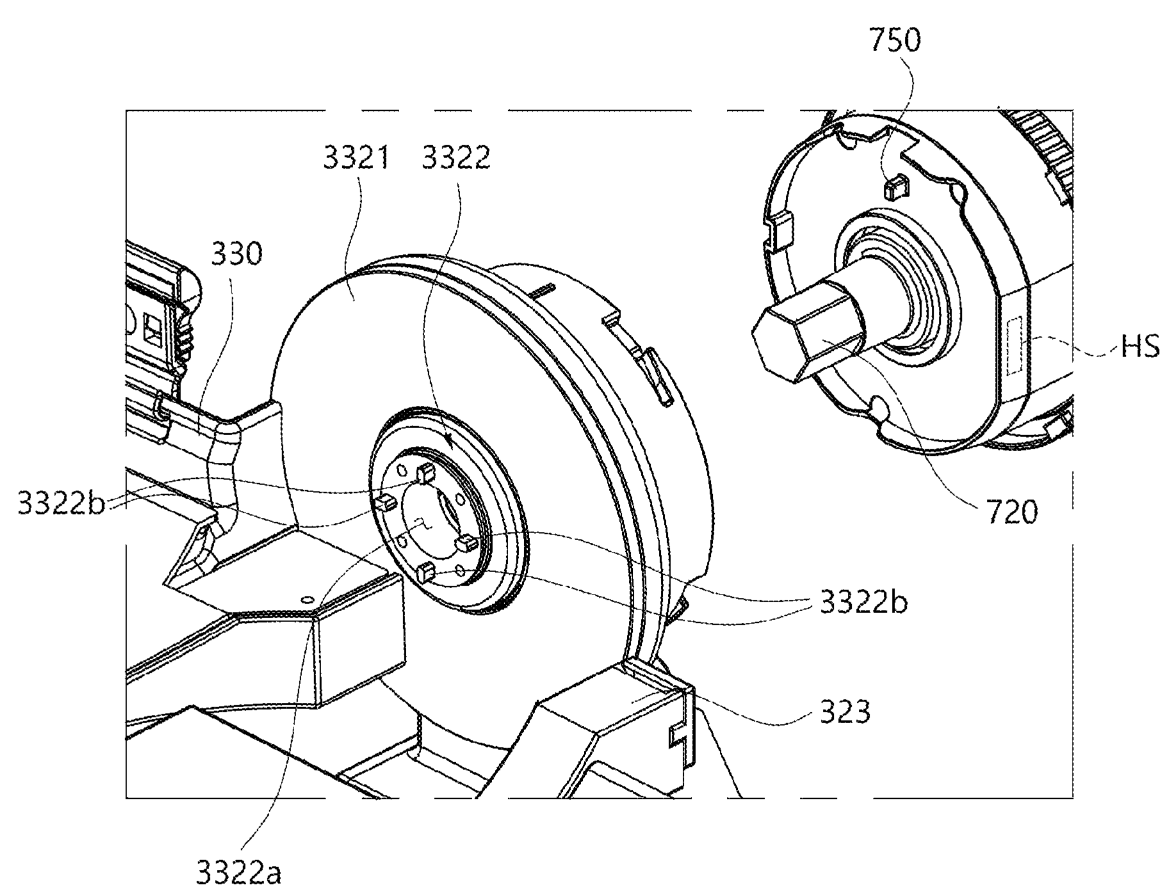

[FIG. 26]
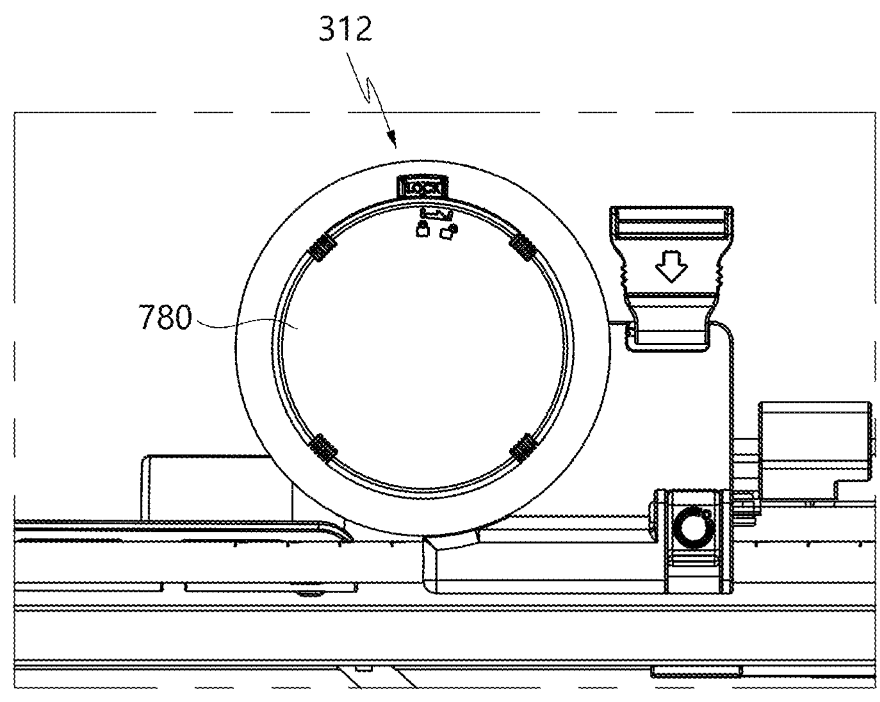

[FIG. 27]
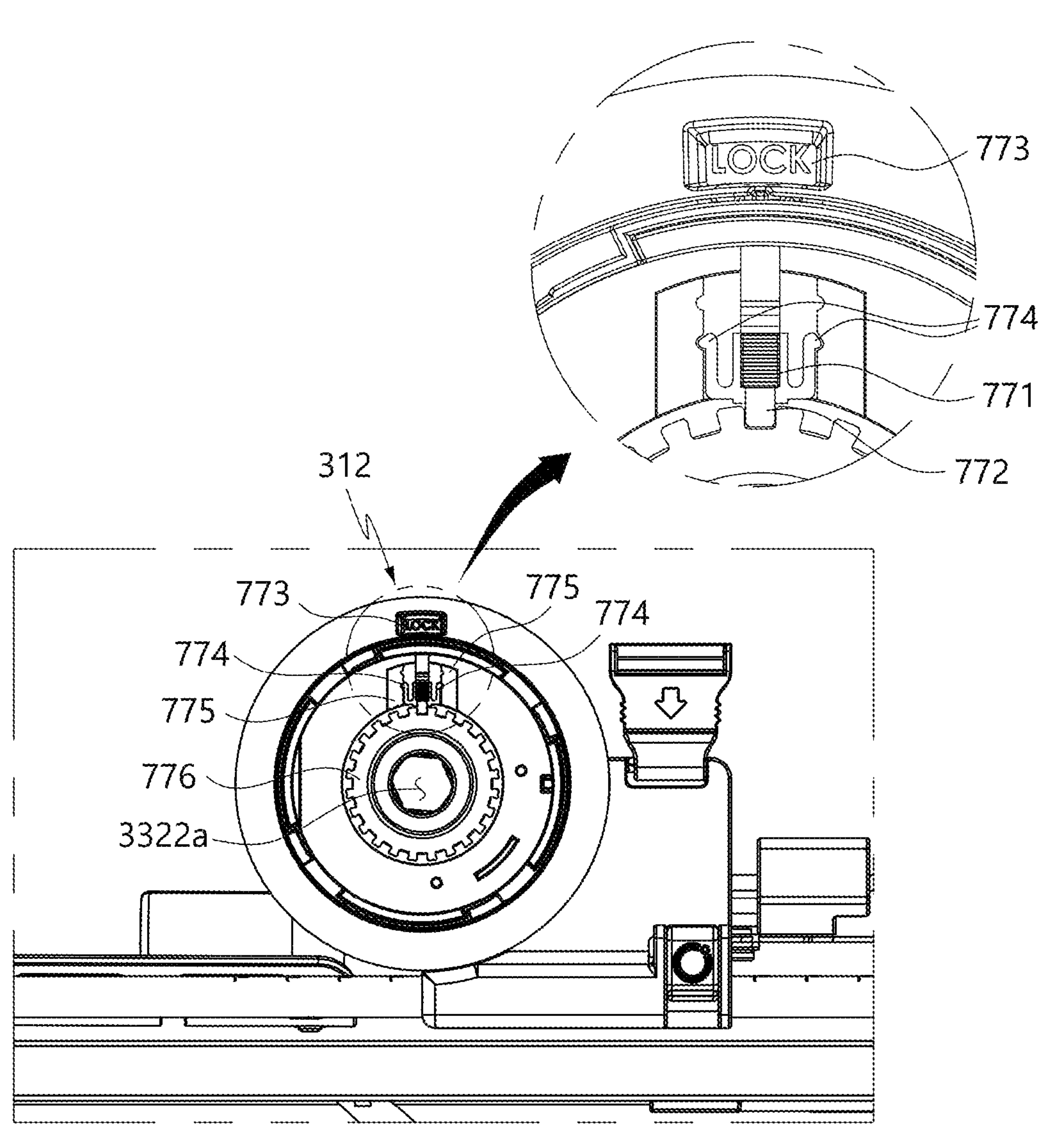

[FIG. 28]
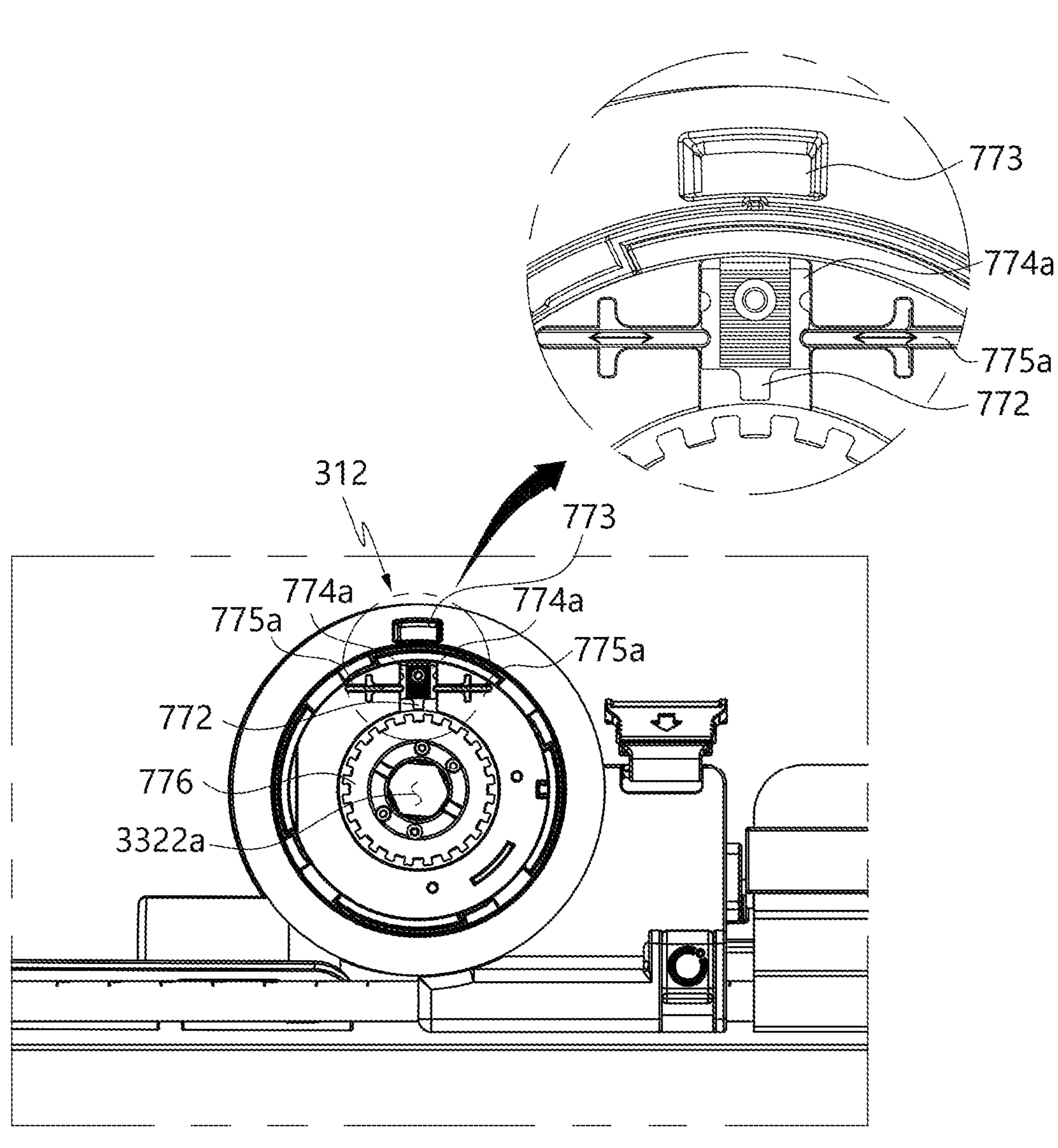

[FIG. 29]
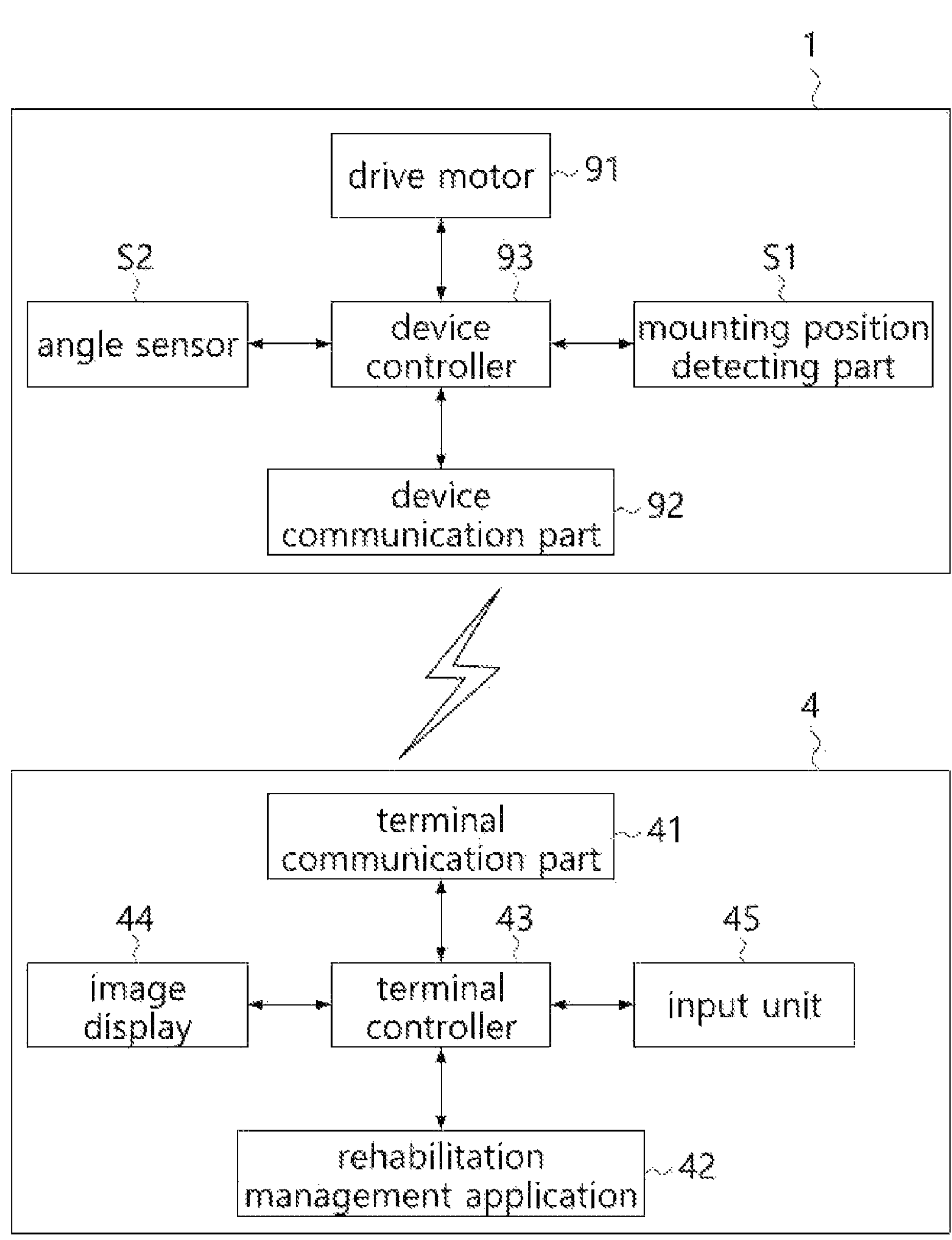

[FIG. 30]
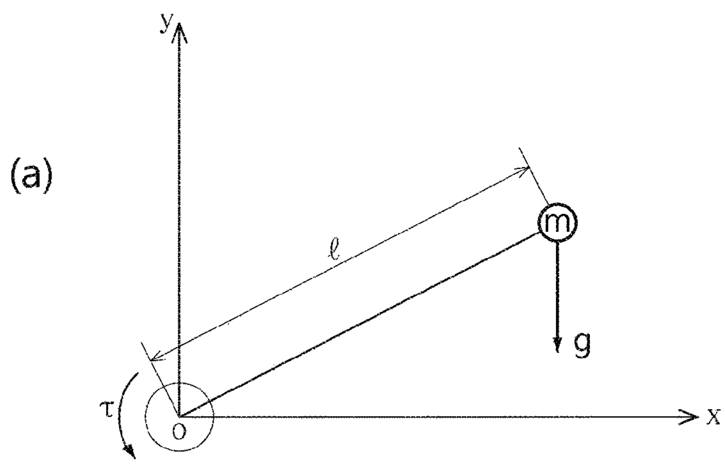
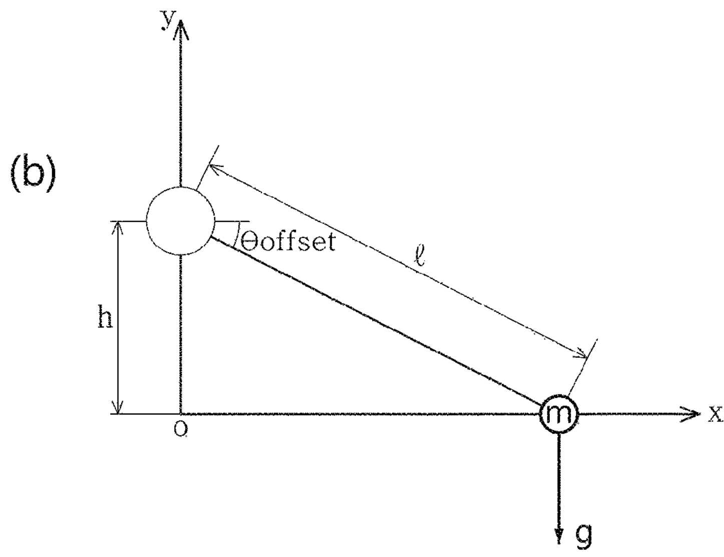

[FIG. 31]
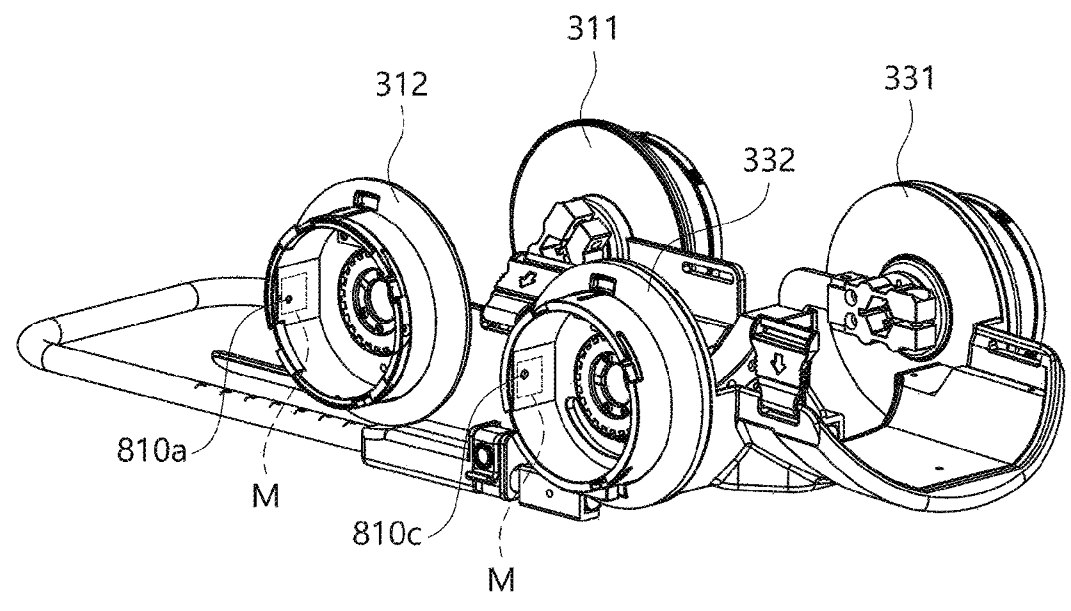

[FIG. 32]
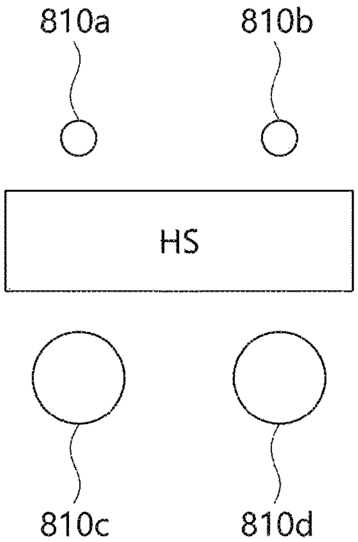

REHABILITATION EXERCISE DEVICE FOR UPPER AND LOWER LIMBS

CROSS REFERENCE TO RELATED APPLICATION

The present application is the U.S. national stage application of International Application No. PCT/KR2021/000439, filed Jan. 13, 2021, which claims priority to Korean Patent Application No. 10-2021-0004009, filed Jan. 12, 2021, Korean Patent Application No. 10-2020-0141794, filed Oct. 29, 2020, and Korean Patent Application No. 10-2020-0022972, filed Feb. 25, 2020, the entire contents of which is incorporated herein for all purposes by this reference.

BACKGROUND OF THE INVENTION

Field of the Invention

The present disclosure relates generally to a rehabilitation exercise device for upper and lower limbs. More particularly, the present disclosure relates to a rehabilitation exercise device for upper and lower limbs, capable of enabling a user to perform an upper or lower limb rehabilitation exercise by placing his/her upper or lower limb thereon.

Description of the Related Art

In general, each joint of a human body has a structure in which neighboring parts of the joint are rotatable with respect to the joint.

Meanwhile, people such as the elderly or rehabilitation patients with weak muscles have difficulty in moving their joints normally compared to healthy people, and even though they need exercise, it is difficult for them to exercise with typical exercise equipment in reality.

When a muscle is weakened or a damaged joint is left unattended over time, the muscle or joint becomes gradually stiff, causing pain when moving, which may interfere with normal activities even when damaged nerves recover.

In addition, patients who have undergone wrist and/or shoulder joint surgery have difficulty exercising by themselves, so joints of the wrist and/or shoulder may become stiff as muscles are weakened and nutrition supply is poor.

Thus, in order to prevent joint deformity and return to normal activities, affected people need to perform rehabilitation exercises accompanied by pain for a long period of time.

In an effort to solve this problem, as a related-art rehabilitation exercise device for enabling the elderly or rehabilitation patients with weak muscles to perform joint exercises through passive rehabilitation, a robotic shoulder apparatus for stroke patient's rehabilitation has been disclosed in Korean Patent No. 10-1163903.

Such a rehabilitation exercise device disclosed in the related art has an unnecessarily complex structure, and thus is problematic in that it is difficult to provide benefits to more users because they need to bear the cost of purchase and installation. In addition, the rehabilitation exercise device is difficult to move, so most users need to move for exercise to the place where the device is located, which is cumbersome.

The foregoing is intended merely to aid in the understanding of the background of the present disclosure, and is not intended to mean that the present disclosure falls within the purview of the related art that is already known to those skilled in the art.

DOCUMENTS OF RELATED ART (Patent document 1) Korean Patent No. 10-1163903 (Title of invention: robotic shoulder apparatus for stroke patient's rehabilitation, registration date: 2012 Jul. 2)

SUMMARY OF THE INVENTION

Accordingly, the present invention was made keeping in mind that the above problems and an object of the present invention is to provide a rehabilitation exercise system for upper and lower limbs capable of doing a rehabilitation exercise by easily adjusting a holing angle of upper limbs or lower limbs according to the rehabilitation patient's condition.

Also, another object of the present invention is to provide a rehabilitation exercise system for upper and lower limbs capable of doing a rehabilitation exercise more efficiently by connecting a rehabilitation exercise device to an information processing terminal such as a smart phone via a wireless communication network and controlling a rehabilitation exercise load of the rehabilitation exercise device based on the first information detected by the rehabilitation exercise device and the second information transmitted from the information processing terminal.

Moreover, yet another object of the present invention is to provide a rehabilitation exercise system for upper and lower limbs controlled in such a manner that for an active exercise during rehabilitation exercise, load applied by a weight of the rehabilitation exercise device or a weight of a user's hand or arm is not felt.

In order to achieve the above objective, according to one aspect of the present disclosure, there is provided a rehabilitation exercise system for upper and lower limbs, comprising: a rehabilitation exercise device for rehabilitation of alms or legs, and an information processing terminal which is connected to the rehabilitation exercise device via a wireless communication network; wherein the rehabilitation exercise device comprises at least one type of sensors which detect a first information; wherein the information processing terminal is configured to transmit a second information to the rehabilitation exercise device via the wireless communication network; wherein the rehabilitation exercise device is configured to control a rehabilitation exercise load based on the first information and the second information.

Here, the rehabilitation exercise device comprises: a rehabilitation exercise unit; and a holder on which the rehabilitation exercise unit is located and configured to support the rehabilitation exercise unit so as to move between a first position on which the rehabilitation exercise unit rests and a second position where the rehabilitation exercise unit is elevated at a predetermined angle; the sensors comprise an angle sensor which detects an angle of the rehabilitation exercise device with respect to a gravity direction according to a state of being supported by the holder.

Furthermore, the rehabilitation exercise unit comprises: a first support for supporting a hand or a foot; a second support for supporting a forearm of an upper limb or a calf of a lower limb; a pair of first hinges for rotatably connecting the first support and the second support; a third support for supporting an upper arm of an upper limb or a thigh of a lower limb; a pair of second hinges for rotatably connecting the second support and the third support; a drive module selectively mounted on any one of the pair of first hinges and the pair of second hinges, a drive motor which pivots the first support or the second support being embedded in the drive module; and a device controller for controlling a torque of the drive motor based on the first information and the second information to control a rehabilitation exercise load. Also, the sensor further comprises a mounting position detecting part which detects a location where the drive module is mounted on the pair of first hinges or the pair of second hinges.

Furthermore, during the operation in an active mode, the device controller is configured to control the drive motor based on the first information and the second information so as to compensate a torque applied to the pair of first hinges or the pair of second hinges for the rehabilitation in the active mode.

Furthermore, the first information comprises a mounting position information of the drive module detected by the mounting position detecting part and a gravity direction angle detected by the angle sensor. Also, the second information comprises: a user's weight corresponding to a weight of the upper limb or the lower limb applied to the rehabilitation exercise unit; and a user's distance which is a distance from a rotation axis of the drive motor to a weight center corresponding to the user's weight.

Furthermore, during the operation in the active mode, the device controller is configured to control the drive motor based on the following formula: $\tau_m=\tau_f(\dot{\theta})+m_h g l_h \cos\theta+m_d g l_d \cos\theta$. Here, $\tau_m$ represents a output torque of the drive motor controlled by the device controller, $\tau_f(\dot{\theta})$ is a pre-registered constant which represents a friction force torque caused by a friction force generated when the first hinges and the second hinges pivot, $m_h$ represents the user's weight, $l_h$ represents the user's distance, $m_d$ is a pre-registered constant which represents a device weight of the rehabilitation exercise unit, $l_d$ represents a device distance value which is a distance from a rotation axis of the drive motor to a weight center corresponding to the device weight, and $\theta$ represents a control rotation angle of the drive motor. Also, $\theta$ is determined by the following formula: $\theta=\alpha\theta_{motor}+\theta_{offset}$. Here, $\alpha$ represents a rotation direction value of the motor set according to the mounting position information and is set as 1 or −1 based on the left side or the right side at the pair of the first hinges or the pair of the second hinges, $\theta_{motor}$ is an absolute rotation angle of the drive motor, and $\theta_{offset}$ is the gravity direction angle.

Furthermore, the second support has adjustable length; the device distance according to the length adjustment of the second support is measured and registered as the first information, or is transmitted from the information processing terminal to the rehabilitation exercise device and registered as the second information.

Furthermore, the mounting position detecting part comprises: a to-be-detected module installed on each of the pair of first hinges and the pair of second hinges; and a sensor module installed on the drive module and configured to recognize the to-be-detected module when the drive module is mounted on any of the pair of first hinges and the pair of second hinges. Here, the to-be-detected module installed on each of the pair of first hinges and the pair of second hinges is configured to be distinguishably recognized.

Furthermore, the sensor module comprises a Hall sensor; each of the to-be-detected module comprises magnet members embedded in the first hinges and the second hinges at positions corresponding to each other; and a magnet hole formed in the first hinges and the second hinges to allow exposure of the magnet member to outside. Also, each magnet hole is configured to differ in at least one of position and size so that the mounting position is distinguishably recognized by the Hall sensor.

Furthermore, the to-be-detected module is installed on the first hinges and the second hinges and comprises a short-range communication tag in which information about the corresponding position is embedded; and the sensor module comprises a reader which recognizes information stored in the tag when the drive module is mounted on the first hinges or the second hinges.

BRIEF DESCRIPTION OF THE DRAWINGS

The above and other objectives, features, and other advantages of the present disclosure will be more clearly understood from the following detailed description when taken in conjunction with the accompanying drawings, in which:

FIG. 1 is a view illustrating a rehabilitation exercise system for upper and lower limbs according an embodiment of the present disclosure;

FIG. 2 is a perspective view illustrating a rehabilitation exercise device for upper and lower limbs according to an embodiment of the present disclosure;

FIG. 3 is a view illustrating a state in which a base plate illustrated in FIG. 2 is tilted from a mounting plate;

FIG. 4 is a view illustrating a state of rehabilitating an upper limb using the rehabilitation exercise device according to the embodiment of the present disclosure;

FIG. 5 is a view illustrating a state of rehabilitating a lower limb using the rehabilitation exercise device according to the embodiment of the present disclosure;

FIG. 6 is a perspective view illustrating a rehabilitation exercise unit illustrated in FIG. 1;

FIGS. 7A and 7B are plan views of FIG. 6 illustrating a length adjustment process of a second support according to the present disclosure;

FIG. 8 is a view illustrating the mechanism for operating the second support illustrated in FIGS. 7A and 7B;

FIG. 9 is a main part enlarged sectional view illustrating a length stopper illustrated in FIGS. 7A and 7B;

FIG. 10 is a view illustrating another embodiment of a length adjustment process of a second support according to the present disclosure;

FIG. 11 is a main part enlarged perspective view illustrating a rotation stopper illustrated in FIG. 10;

FIG. 12 is a perspective view illustrating a restraining dial illustrated in FIG. 11;

FIG. 13 is a main part enlarged sectional view of FIG. 10;

FIG. 14 is a main part enlarged perspective view illustrating a state in which the mounting plate illustrated in FIG. 2 is erected at a predetermined angle with respect to the base plate;

FIG. 15 is a view illustrating the mechanism for operating the mounting plate illustrated in FIG. 14;

FIG. 16 is a main part enlarged view of FIG. 14;

FIG. 17 is a main part enlarged side view illustrating the mounting plate illustrated in FIG. 13;

FIG. 18 is a main part enlarged perspective view of FIG. 13;

FIG. 19 is a main part enlarged perspective view illustrating the mounting plate according to the present disclosure as viewed in another direction;

FIG. 20 is a view illustrating the structure of a catching protrusion illustrated FIG. 19;

FIG. 21 is a main part enlarged perspective view illustrating the mounting plate according to the present disclosure as viewed in another direction;

FIG. 22 is a perspective view illustrating a drive module according to the present disclosure;

FIG. 23 is an enlarged perspective view illustrating a drive shaft fixing member illustrated in FIG. 22;

FIGS. 24 and 25 are views illustrating the principle of mounting the drive module according to the present disclosure;

FIGS. 26 to 28 are views illustrating a rotation restraining part according to the present disclosure;

FIG. 29 is a view illustrating control block diagrams for the rehabilitation exercise device 1 and the information processing terminal 4 according to the embodiment of the present disclosure;

FIG. 30 is a view illustrating elements which affect a rehabilitation exercise load in the rehabilitation exercise system for upper and lower limbs according to the embodiment of the present disclosure; and FIGS. 31 and 32 are views illustrating a mounting position detecting part according to the present disclosure.

DETAILED DESCRIPTION OF THE INVENTION

The present disclosure relates to a rehabilitation exercise device for upper and lower limbs. The rehabilitation exercise device is characterized by including: a base plate; a mounting plate on which a rehabilitation exercise unit is mounted, the rehabilitation exercise unit including a first support for supporting a user's hand or foot, a second support for supporting a user's forearm or calf, a third support for supporting a user's upper arm or thigh, the mounting plate having a first side that is coupled to the base plate to be horizontally movable along a plate surface thereof; and a link member having opposite sides that are rotatably coupled to the base plate and the mounting plate, respectively, and configured to adjust an angle between the base plate and the mounting plate by being rotated when the first side of the mounting plate is moved horizontally along the plate surface of the base plate.

The above and other objectives, features, and advantages of the present disclosure will be more clearly understood from the following detailed description when taken in conjunction with the accompanying drawings. However, it should be understood that the various changes to the following embodiments are possible and the scope of the present disclosure is not limited to the following embodiments. The embodiments of the present disclosure are provided for allowing those skilled in the art to more clearly comprehend the present disclosure, and the scope of the present disclosure should be defined by the appended claims.

Terms used in this specification are selected to describe embodiments and thus should not be construed as the limit of the present disclosure. An element expressed in a singular form in this specification may be plural elements unless it is necessarily singular in the context. The terms "comprise" and/or "comprising" when used in this specification, specify the presence of stated features, but do not preclude the presence or addition of one or more other features. The same reference numerals are used throughout the different drawings to designate the same or similar components. The expression "and/or" is interpreted to include each of enumerated items, and all combinations including one or more items selected from among the enumerated items. Although the terms "first", "second", etc. may be used herein to describe various elements, these elements should not be limited by these terms. These terms are only used to distinguish one element from another element. For example, a first element discussed below could be termed a second element without departing from the scope of the present disclosure.

Unless otherwise defined, all terms including technical and scientific terms used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Hereinafter, the present disclosure will be described in detail with reference to the accompanying drawings.

FIG. 1 is a view illustrating a rehabilitation exercise system for upper and lower limbs according an embodiment of the present disclosure.

As shown in FIG. 1, the rehabilitation exercise system for upper and lower limbs according the embodiment of the present disclosure comprises an information processing terminal 4 and a rehabilitation exercise device 1.

The information processing terminal 4 is connected to the rehabilitation exercise device 1 via a wireless communication network 6 to communicate with each other. As an example, in the present invention, a Wi-Fi network or a Bluetooth network is used for the wireless communication network 6, but the wireless communication is not limited thereto.

The information processing terminal 4 can be configured in various form which operates based on an operating system. For example, the information processing terminal 4 may comprise a mobile terminal such as a smart phone, a tablet, etc. and also may comprise a PC such as a desktop or a laptop. Here, details about the information processing terminal 4 will be described later.

FIG. 2 is a perspective view of the rehabilitation exercise device according to the embodiment of the present invention and FIG. 3 is a view illustrating that the rehabilitation exercise device according to the embodiment of the present invention is elevated by an angle of a holder.

As illustrated in FIGS. 2 and 3, the rehabilitation exercise device 1 according to the embodiment of the present disclosure includes a rehabilitation exercise unit 3 and a holder 5 for supporting the rehabilitation exercise unit 3.

The rehabilitation exercise unit 3 may include: a first support 310 for supporting a user's hand or foot; a second support 320 for supporting a user's forearm or calf; a pair of first hinges 311 and 312 for rotatably connecting the first support 310 and the second support 320 to each other; a third support 330 for supporting a user's upper arm or thigh; and a pair of second hinges 331 and 332 for rotatably connecting the second support 320 and the third support 330 to each other.

The holder 5 includes a base plate 510, and a mounting plate 520 on which the rehabilitation exercise unit 3 is mounted. The base plate 510 and the mounting plate 520 adopt a link-mechanism that converts horizontal motion into vertical motion. The link-mechanism is such that a first side of the mounting plate 520 is installed on the base plate 510 to be horizontally movable along a plate surface thereof, an intermediate region of the mounting plate 520 is connected to a first side of a link member 530, and a second side of the link member 530 is rotatably installed on the base plate 510.

According to the above configuration, as illustrated in FIG. 2, in a state in which the mounting plate 520 is folded to the base plate 510, as illustrated in FIG. 4, upper limb rehabilitation exercise is performed. On the other hand, as illustrated in FIG. 3, in a state in which the mounting plate 520 is erected at a certain angle from the base plate 510 by the link mechanism, as illustrated in FIG. 4, lower limb rehabilitation exercise is performed.

Here, angle adjustment between the mounting plate 520 and the base plate 510, and angle fixing and releasing will be described later.

The rehabilitation exercise unit 3 according to the present disclosure includes a distance adjustment part for adjusting the distance between the first support 310 and the third support 330 by adjusting the length of the second support 320 according to application in an upper or lower limb, and the length of a rehabilitation patient's upper or lower limb.

The distance adjustment part of the rehabilitation exercise unit 3 according to the present disclosure will be described with reference to FIGS. 6 to 9.

The rehabilitation exercise unit 3 according to the present disclosure, as an example, adopts a stacked slide-crank structure to the second support 320 so that the length of the second support 320 supporting the forearm or the calf is adjusted.

The second support 320 may include a first fixing plate 322, a second fixing plate 323, a first moving plate 324, a second moving plate 325, and a hinge shaft 321.

The first fixing plate 322 is connected to the pair of first hinges 311 and 312 to be rotatably coupled to the first support 310. The second fixing plate 323 is connected to the pair of second hinges 331 and 332 to be rotatably coupled to the third support 330.

The first moving plate 324 is provided between the first fixing plate 322 and the hinge shaft 321 and is movable reciprocally therebetween.

The second moving plate 325 is provided between the second fixing plate 323 and the hinge shaft 321 and is movable reciprocally therebetween.

The hinge shaft 321 is provided between the first fixing plate 322 and the second fixing plate 323.

Meanwhile, the distance adjustment part includes a first crank 326 and a second crank 327.

The first crank 326 is rotatably connected to the first fixing plate 322 and the hinge shaft 321 to convert a rotary motion of the hinge shaft 321 into a linear motion of the first fixing plate 322.

The first crank 326 includes a first adjustment link 326*a*, a second adjustment link 326*b*, and a first connection link 326*c*. The first adjustment link 326*a* is rotatably coupled to the hinge shaft 321.

The second adjustment link 326*b* has a first side rotatably coupled to the first adjustment link 326*a*, and a second side rotatably coupled to the first fixing plate 322.

The first connection link 326*c* is rotatably coupled to the first moving plate 324 and an intermediate region of the first adjustment link 326*a*.

The second crank 327 is rotatably connected to the second fixing plate 323 and the hinge shaft 321 to convert a rotary motion of the hinge shaft 321 into a linear motion of the second fixing plate 323.

The second crank 327 includes a third adjustment link 327*a*, a fourth adjustment link 327*b*, and a second connection link 327*c*.

The third adjustment link 327*a* is rotatably coupled to the hinge shaft 321. The third adjustment link 327*a* is disposed opposite to the first adjustment link 326*a* at an angle of 180 degrees.

The fourth adjustment link 327*b* has a first side rotatably coupled to the third adjustment link 327*a*, and a second side rotatably coupled to the second fixing plate 323. The fourth adjustment link 327*b* is disposed opposite to the second adjustment link 326*b*.

The second connection link 327*c* is rotatably coupled to the second moving plate 325 and an intermediate region of the third adjustment link 327*a*. The second connection link 327*c* is disposed opposite to the first connection link 326*c*.

Meanwhile, reciprocating movement of the first moving plate 324 is guided by a pair of first guide rods 329*a* extending in length from the first fixing plate 322 toward the first moving plate 324. In addition, reciprocating movement of the first moving plate 324 is guided by a pair of third guide rods 329*c* extending in length from the hinge shaft 321 toward the first moving plate 324. Here, in this embodiment, it is illustrated that the first guide rods 329*a* and the third guide rods 329*c* are provided in pairs, respectively, but the present disclosure is not limited thereto. For example, at least one first guide rod 329*a* and at least one third guide rod 329*c* may be provided.

In addition, reciprocating movement of the second moving plate 325 is guided by a pair of second guide rods 329*b* extending in length from the second fixing plate 323 toward the second moving plate 325. In addition, reciprocating movement of the second moving plate 325 is guided by a pair of third guide rods 329*c* extending in length from the hinge shaft 321 toward the second moving plate 325. Here, in this embodiment, it is illustrated that the second guide rods 329*b* and the third guide rods 329*c* are provided in pairs, respectively, but the present disclosure is not limited thereto. For example, at least one second guide rod 329*b* and at least one third guide rod 329*c* may be provided.

According to the configuration as described above, in the distance adjustment part of the rehabilitation exercise device 1 according to the present disclosure, as illustrated in FIG. 7, by implementing the slide-crank mechanism in which the first fixing plate 322 and the first moving plate 324, and the second fixing plate 323 and the second moving plate 325 are operated in conjunction with each other, respectively, so as to be mutually approached or spaced apart with respect to the hinge shaft 321, it is possible to adjust the length of the second support 320, thereby adjusting the distance between the first support 310 and the third support 330.

Hereinafter, in order to help the understanding of the present disclosure, the adjustment of the length of the second support 320 will be described in detail with reference to FIG. 8.

In FIG. 8, when the first adjustment link 326*a* and the second adjustment link 326*b* are pivoted clockwise around the hinge shaft 321, the angle between the first adjustment link 326*a* and the second adjustment link 326*b* and the angle between the first adjustment link 326*a* and the first connection link 326*c* increase, so that the distance between the hinge shaft 321 and the first fixing plate 322 is increased. Similarly, the angle between the third adjustment link 327*a* and the fourth adjustment link 327*b*, and the angle between the third adjustment link 327*a* and the second connection link 327*c* increase to the same angle as that between the first adjustment link 326*a* and the second adjustment link 326*b*, so that the distance between the hinge shaft 321 and the second fixing plate 323 is increased. Consequently, the first fixing plate 322 and the second fixing plate 323 are spaced apart from each other by equal distances from the hinge shaft 321.

On the contrary, in FIG. 8, when the first adjustment link 326*a* and the second adjustment link 326*b* are pivoted counterclockwise around the hinge shaft 321, the angle between the first adjustment link 326*a* and the second adjustment link 326*b* and the angle between the first adjustment link 326*a* and the first connection link 326*c* decrease, so that the distance between the hinge shaft 321 and the first fixing plate 322 is decreased. Similarly, the angle between the third adjustment link 327*a* and the fourth adjustment link 327*b*, and the angle between the third adjustment link 327*a* and the second connection link 327*c* decreased to the same angle as that between the first adjustment link 326*a* and the second adjustment link 326*b*, so that the distance between the hinge shaft 321 and the second fixing plate 323 is decreased. Consequently, the first fixing plate 322 and the second fixing plate 323 are approached to each other by equal distances from the hinge shaft 321.

Therefore, in the rehabilitation exercise device 1 according to the present disclosure, the first fixing plate 322 and the first moving plate 324, and the second fixing plate 323 and the second moving plate 325 are operated in conjunction with each other, respectively, so as to be mutually approached or spaced apart with respect to the hinge shaft 321.

Meanwhile, the first fixing plate 322 and the second fixing plate 323 are connected to each other by a pair of connection bars 328.

In the present disclosure, a side of each of the connection bars 328 is fixed to the second fixing plate 323, and the first fixing plate 322 is movably coupled to the connection bars 328, so that the first fixing plate 322 is approached to and spaced apart from the second fixing plate 323.

A through-hole 322*a* (see FIG. 9) for allowing passage of each of the connection bars 328 therethrough may be formed in the first fixing plate 322, so that longitudinal movement of the first fixing plate 322 may be guided along the connection bar 238.

In addition, a length stopper 340 may be installed on the first fixing plate 322 to restrain the longitudinal movement of the first fixing plate 322, for example, to limit relative movement of the first fixing plate 322 and the second fixing plate 323. In the present disclosure, as an example, a pair of length stoppers 340 are installed on the pair of connection bars 328, respectively.

FIG. 9 is a sectional view illustrating the region of the length stopper 340 according to the present disclosure. Referring to FIG. 9, the length stopper 340 may include a restraining lever 341 and a pressurizing member 345.

The restraining lever 341 is rotatably installed on a rotary shaft 322*b* coupled to the first fixing plate 322.

The restraining lever 341 includes a pusher 342 provided at a first end thereof to pressurize or release the pressurizing member 345, and a knob 343 provided at a second end thereof to rotate the pusher 342 to allow the pusher 342 to pressurize or release the pressurizing member 345.

The pusher 342 has a semicircular arc shape having a predetermined radius of curvature, and is configured to be brought into contact with and spaced apart from the pressurizing member 345 by rotation.

Therefore, in FIG. 9, when the restraining lever 341 is rotated clockwise around the rotary shaft 322*b*, the pusher 342 is rotated toward the pressurizing member 345 to be brought into contact with the pressurizing member 345 and to pressurize the pressurizing member 345, and the pressurizing member 345 pressurizes the connection bar 328 passing through the through-hole 322*a* to prevent the first fixing plate 322 from moving in the longitudinal direction. On the other hand, when the restraining lever 341 is rotated counterclockwise around the rotary shaft 322*b*, the pusher 342 is spaced from the pressurizing member 345 and releases the pressurizing member 345, so that the connection bar 238 is allowed to be moved inside the through-hole 322*a*, thereby allowing the movement of the first fixing plate 322 in the longitudinal direction along the connection bar 328.

Here, in this embodiment, it is illustrated that a side of the connection bar 328 is fixed to the second fixing plate 323, and the first fixing plate 322 is movably coupled to the connection bar 328, but the present disclosure is not limited thereto. For example, the side of the connection bar 328 may be fixed to the first fixing plate 322, and the second fixing plate 323 may be movably coupled to the connection bar 328. In this case, the restraining lever 341 is provided on the second fixing plate 323.

FIGS. 10 to 13 are views illustrating an example of a structure for restraining longitudinal movement of a second support 320 according to another embodiment of the present disclosure. A rehabilitation exercise unit 3 according to the other embodiment of the present disclosure may include a rotation stopper 350 provided on a hinge shaft 321 to limit relative movement of a first fixing plate 322 and a second fixing plate 323.

As described above, the second support 320 according to the present disclosure has a slide-crank structure in adjusting a longitudinal length thereof, which includes rotation of the hinge shaft 321. The rotation stopper 350 restrains the rotation of the hinge shaft 321 to maintain a predetermined length.

The rotation stopper 350 includes a restraining dial 351, a shaft body 353 for forming the hinge shaft 321, a shaft column 354 protruding upward from the shaft body 353, and a shaft plate 352 rotated around the shaft body 354 and connected to the first adjustment link 326*a* and the third adjustment link 327*a* to rotate the first adjustment link 326*a* and the third adjustment link 327*a* with respect to the shaft body 353.

The restraining dial 351 includes a restraining pin 351*a* and a catching recess 351*c*.

The restraining pin 351*c* is formed by protruding from an end of the restraining dial 351 oriented toward the shaft body 353, and is inserted into or released from any one selected from among a plurality of restraining holes 352*a* which will be described later.

The catching recess 351*c* is depressed in a region of the end of the restraining dial 351 oriented toward the shaft body 353, at a position spaced from the restraining pin 351*a*. In this embodiment, a pair of catching recesses 351*c* are provided opposite to each other.

The plurality of restraining holes 352*a* are formed in the shaft body 353 at a predetermined interval along the circumferential direction of the shaft column 354.

The shaft plate 352 has a circular ring shape. The shaft plate 352 is configured such that the first adjustment link 326*a* and the third adjustment link 327*a* are connected to an outer circumference thereof, and the restraining dial 351 is rotatably provided on an inner circumference thereof. In addition, the shaft plate 352 has a pair of catching protrusions 352*b* protruding from a region of the inner circumference thereof, and connecting the restraining dial 351 to the shaft plate 352 by being caught by the catching recesses 351*c* of the restraining dial 351.

In addition, the rotation stopper 350 according to the present disclosure may further include an elastic member 355.

The elastic member 355 is provided between the shaft column 354 and the restraining dial 351, and generates elastic force acting on the restraining dial 351 so that the restraining pin 351*a* is inserted into the selected restraining hole 352*a*.

When a user wants to adjust the length of the second support 320, the user adjusts the length by pulling the restraining dial 351 upward so that the restraining dial 351 ascends from the shaft body 353 to a position where the restraining pin 351*a* is separated from the restraining hole 352*a*. Then, when the second support 320 is adjusted to a desired length, the user releases the restraining dial 351 so that the restraining dial 351 descends toward the shaft body 353 by the elastic force of the elastic member 355, and at the same time, the restraining pin 351*a* is inserted into the restraining hole 352*a* at a corresponding position.

With this configuration, in the rotation stopper 350 according to the present disclosure, when the restraining pin 351*a* is inserted into the restraining hole 352*a*, the shaft plate 352 is not rotated with respect to the shaft body 353, so that the length of the second support 320 is not allowed to be adjusted. At the same time, the catching protrusions 352*b* of the shaft plate 352 are caught by the catching recesses 351*c* of the restraining dial 351, so that the restraining dial 351 is prevented from being rotated around the shaft column 354.

On the other hand, in the rotation stopper 350 according to the present disclosure, when the dial pin 351*a* is released from the restraining hole 352*a*, the shaft plate 352 is rotated with respect to the shaft body 353, so that the length of the second support 320 is allowed to be adjusted. At this time, the catching protrusions 352*b* of the shaft plate 352 are maintained caught by the catching recesses 351*c* of the restraining dial 351, so that the restraining dial 351 is maintained in a state connected to the shaft plate 352. Thus, the restraining dial 351 is allowed to be rotatable forward and backward around the shaft column 354, so that the first fixing plate 322 and the second fixing plate 323 are mutually approached or spaced apart with respect to the shaft body 353, thereby adjusting the length of the second support 320.

In FIG. 12, reference numeral 351*b* denotes a pin insertion portion into which the restraining pin 351*a* is inserted and fixed, and reference numeral 351*d* denotes a shaft through-hole through which the shaft column 354 passes and fixed. For convenience of explanation, FIG. 11 illustrates a state in which the restraining pin 351*a* is inserted in the restraining hole 352*a* in a state of being released from the restraining dial 351.

As such, by implementing a slide-crank mechanism in which the first fixing plate 322 and a first moving plate 324, and the second fixing plate 323 and a second moving plate 325 are operated in conjunction with each other, respectively, so as to be mutually approached or spaced apart with respect to the hinge shaft 321, it is possible to adjust the length of the second support 320, thereby adjusting the distance between the first support 310 and the third support 330 in response to various lengths of the forearm or calf of the user during rehabilitation.

Hereinafter, the configuration of the holder 5 according to the present disclosure will be described in detail with reference to FIGS. 14 to 21.

As described above, the holder 5 may include the base plate 510, the mounting plate 520, and the link member 530. According to this configuration, a link mechanism as illustrated in FIG. 15 is implemented.

As described above, the opposite sides of the link member 530 are rotatably coupled to the base plate 510 and the mounting plate 520, respectively. Here, the first side (i.e., in the direction of the first support 510) of the mounting plate 520 is coupled to the base plate 510 to be horizontally movable along the plate surface thereof, and the first side of the link member 530 is rotatably coupled to the intermediate region of the mounting plate 520. In addition, a second side of the mounting plate 520 is approached to and spaced apart from the base plate 510 in the vertical direction by the link mechanism, so that angle adjustment is implemented as illustrated in FIGS. 2 and 3.

The second side of the link member 530 is rotatably coupled to a fixing shaft 531 provided on the base plate 510, so that when the first side of the mounting plate 520 moves in the horizontal direction, the angle of the mounting plate 520 is adjusted by rotation of the opposite sides of the link member 530.

Meanwhile, a pair of extension brackets 521 are installed opposite at the first side of the mounting plate 520 by extending parallel toward the third support 330. First ends of the pair of extension brackets 521, for example, first ends thereof oriented toward the first support 310, are rotatably coupled to the mounting plate 520. Second ends of the pair of extension brackets 521, for example, second ends thereof oriented toward the third support 330, are connected to each other by a connection rod 522.

In addition, a catching plate 511 is installed inside the base plate 510, with a plurality of catching protrusions 512 formed thereon along the longitudinal direction and allowing the connection rod 522 to be caught thereby in response to the angle between the mounting plate 520 and the base plate 510. The plurality of catching protrusions 512 are formed at a predetermined interval along the longitudinal direction of the pair of extension brackets 521, so that the connection rod 522 is selectively caught by the catching protrusions 512. Thus, in response to an inclination angle between the mounting plate 520 and the base plate 510, the connection rod 522 is caught by any one of the catching protrusions 512, so that the inclination angle is maintained at a predetermined angle.

In addition, the holder 5 according to the present disclosure may include a fixing unit 540 for fixing the connection rod 522 to maintain the connection rod 522 caught by any one of the catching protrusions 512.

In the embodiment of the present disclosure, as an example, as illustrated in FIGS. 16 and 17, the base plate 510 includes a plurality of restraining recesses 513*a* and a moving hole 513*b*.

The plurality of restraining recesses 513*a* are depressed in a side surface of the base plate 510 at respective positions corresponding to the catching protrusions 512. In other words, the plurality of restraining recesses 513*a* are arranged at a predetermined interval on the side surface of the base plate 510 along the longitudinal direction thereof in correspondence with the catching protrusions 512 arranged along the longitudinal direction of the extension brackets 521.

The moving hole 513*b* is formed in each of the restraining recesses 513*a* by passing therethrough to be oriented toward a selected catching protrusion 512. In other words, the moving hole 513*b* is formed to pass through an inside and an outside of a plate surface of the base plate 510 at a position where the restraining recess 513*a* is formed.

Here, as illustrated in in FIG. 17, the moving hole 513*b* has a shape that is open diagonally upward to allow insertion or release of an extension unit 542 of a fixing unit 540, which will be described later, into or from the moving hole 513*b*.

As illustrated in FIG. 18, the fixing unit 540 according to an embodiment of the present disclosure may include the extension unit 542 and a unit body 541.

The extension unit 542 has a first side connected to the connection rod 522, and a second side extending outward of the base plate 510 through the moving hole 513*b*. In the present disclosure, as an example, as illustrated in FIG. 21, the first side of the extension unit 542 is connected to the connection rod 522 through an intermediate plate 543. The intermediate plate 543 may be directly fastened to the connection rod 522 or may be connected to the connection rod 522 by being fastened to an associated one of the extension brackets 521 connected to the connection rod 522.

The unit body 541 is coupled to the second side of the extension unit 542. In the present disclosure, as an example, an insertion hole (not illustrated) for allowing insertion of the extension unit 542 therein is formed in the unit body 541 so that the extension unit 542 is inserted into the insertion hole to be coupled to the unit body 541.

In the embodiment of the present disclosure, as an example, the unit body 541 is coupled to the extension unit 542 so as to be movable between a fixing position inserted into the restraining recess 513*a* and a release position released from the restraining recess 513*a*. To this end, as an example, as illustrated in FIG. 18, the extension unit 542 has a pair of operating grooves 542*b* formed at a predetermined interval along the longitudinal direction thereof. In addition, as an example, the unit body 541 has an operating protrusion 541*c* caught by the operating grooves 542*b* at the fixing position and the release position of the unit body 541, respectively.

In the present disclosure, the operating protrusion 541*c* may be configured in a form that is elastically pressurized in the directions of the operating grooves 542*b* so that when the user pulls the unit body 541 in the release direction, the operating protrusion 541*c* caught by an inner operating groove 542*b* is released therefrom and inserted into an outer operating groove 542*b*. On the other hand, when the user pushes the unit body 541 in the fixing direction, the operating protrusion 541*c* caught by the outer operating groove 542*b* is released therefrom and inserted into the inner operating groove 542*b*.

In addition, the unit body 541 includes an insertion portion 541*b* inserted into the restraining recess 513*a* at the fixing position and the release position, and a knob 541*a* operable by the user to move the unit body 541 between the fixing position and the release position. Here, the insertion portion 541*b* is configured in a size that is insertable into the restraining recess 513*a*, preferably in a size that is caught by the moving hole 513*b* without moving thereinto.

According to the configuration as described above, when the user wants to adjust the angle between the base plate 510 and the mounting plate 520, the user pulls the knob 541*a* with the unit body 541 being at the fixing position to allow the unit body 541 to be moved to the release position, so that the insertion portion 541*b* of the unit body 541 is released from the restraining recess 513*a*.

In this state, when the user moves the knob 541*a* diagonally upward, the connection rod 522 connected to the extension unit 542 is released from the catching protrusion 512, and at the same time, the extension unit 542 is moved along the moving hole 513*b* to a position outside the moving hole 513*b*.

In this state, when the user moves the knob 541*a* while adjusting the angle of the mounting plate 520 so that the extension unit 542 is inserted into a moving hole 513*b* associated with a desired angle, the extension unit 542 is inserted into the moving hole 513*b*, and at the same time, the connection rod 522 is caught by an associated one of the catching protrusions 512.

When the angle adjustment is completed as described above, the user pushes back the unit body 541 to allow the insertion portion 541*b* to be inserted into a restraining recess 513*a* associated with the moving hole 513*b*. Then, the insertion portion 541*b* is caught by the moving hole 513*b*, so that the connection rod 522 is fixed to the selected catching protrusion 512.

Meanwhile, as illustrated in FIG. 19, each of the catching protrusions 512 according to an embodiment of the present disclosure may extend to a length corresponding to the length of the connection rod 522 in a direction intersecting the longitudinal direction of the extension brackets 521, i.e., in the longitudinal direction of the connection rod 522.

In addition, as illustrated in FIGS. 19 and 20, each of the catching protrusions 512 according to the embodiment of the present disclosure may be configured such that a side thereof in a direction in which the fixing unit 540 is installed, i.e., a D1 direction in FIG. 20, protrudes relatively more than an opposite side thereof in a D2 direction, in a direction in which catching is released.

As described above, in the embodiment of the present disclosure, as an example, the fixing unit 540 is installed only on a side of the base plate 510. Thus, when the user releases the connection rod 522 from the catching protrusion 512 while moving the fixing unit 540, a lengthwise side of the connection rod 522 in the direction of the fixing unit 540 may be lifted relatively more in the release direction, and an opposite lengthwise side may be lifted relatively less.

Therefore, as illustrated in FIG. 20, by configuring a lengthwise side of the catching protrusion 512 opposite to the direction of the fixing unit 540 to protrude relatively less, in releasing the connection rod 522 from the catching protrusion 512 through manipulation of the fixing unit 540, when catching of the lengthwise side of the connection rod in the direction in which the fixing unit 540 is installed is released, the entire connection rod 522 may be released from the catching protrusion 512.

Meanwhile, as illustrated in FIG. 21, the rehabilitation exercise device 1 for the upper and lower limbs according to the embodiment of the present disclosure may further include an elastic unit 522*f*.

The elastic unit 522*f* provides an elastic force acting in a direction in which the connection rod 522 is maintained caught by the catching protrusion 512, so that the connection rod 522 is prevented from being released from the catching protrusion 512 without a user's manipulation. For example, in a state in which the unit body 541 of the fixing unit 540 is located at the release position due to a process of a user's manipulation or other cause, when the connection rod 522 is released from the catching protrusion 512 due to an external impact or the like, the mounting plate 520 may be rapidly folded in the direction of the base plate 510. Therefore, the release of the connection rod 522 is prevented even with a certain impact, so that a safety accident is prevented from occurring.

In addition, even during the manipulation of the fixing unit 540, the connection rod 522 is in a state of being pressurized in the insertion direction into the catching protrusion 512. Therefore, a force that moves the connection rod 522 in the insertion direction is generated at an insertion position of the connection rod 522, thereby facilitating the insertion of the connection rod 522 into the catching protrusion 512.

This will be described in more detail with reference to FIG. 21. The mounting plate 520 according to an embodiment of the present disclosure may include a moving bracket 526, a pair of mounting brackets 525, and a mounting portion 527.

The moving bracket 526 is installed on the base plate 510 to be horizontally movable along the base plate 510. The pair of mounting brackets 525 are rotatably coupled to opposite sides of the moving bracket 526. Here, each of the pair of link members 530 may be rotatably coupled to an intermediate region of an associated one of the mounting brackets 525. The mounting portion 527 is formed in a plate shape supported by the moving bracket 526 and the mounting brackets 525 to define an upper plate of the mounting plate 520, and allows mounting of the rehabilitation exercise unit 2 thereon.

Here, the extension brackets 521 are rotatably coupled to the opposite sides of the moving brackets 526 so that the moving bracket 526 is moved in conjunction with movement of the extension brackets 521. At this time, the elastic unit **522*f* pressurize at least one of the pair of extension brackets 521 downward in a state of being installed on the moving bracket 526, so that the connection rod 522 coupled to the extension brackets 521 is pressurized in a direction caught by the catching protrusion 512**.

In the present disclosure, as an example, as illustrated in FIG. 21, the elastic unit **522*f* is provided in the form of a plate spring. In addition, the extension bracket 521 has a skirt 522*d* extending inward, so that the elastic unit 522*f* pressurizes the skirt 522*d* to pressurize the extension bracket 521**.

Meanwhile, in the rehabilitation exercise device 1 according to the present disclosure, the drive module 7 may be selectively couple to any one of the pair of first hinges 311 and 312 and the pair of second hinges 331 and 332. For example, in the case of the upper limb, when the drive module 7 is mounted on any one of the first hinges 311 and 312, wrist rehabilitation exercise is possible. On the other hand, when the drive module 7 is mounted on any one of the second hinges 331 and 332, elbow joint rehabilitation exercise is possible.

At this time, in the case of the pair of first hinges 311 and 312, a mounting position of the drive module 7 may be determined according to rehabilitation of a left or right upper limb. Similarly, in the case of the pair of second hinges 331 and 332, the drive module 7 may be selectively mounted according to rehabilitation of a right or left upper limb.

Hereinafter, the drive module 7 according to the present disclosure will be described in detail with reference to FIGS. 22 to 25.

As described above, the drive module 7 is selectively mounted on any one of the pair of first hinges 311 and 312 and the pair of second hinges 331 and 332 to pivot the first support 310 or the second support 320.

The drive module 7 may include a body housing 710 in which components such as a drive motor, a printed circuit board, etc. are accommodated, a drive shaft 720 to which a rotary shaft of the drive motor is connected, and a ring member 730 for allowing mounting and fixing of the drive module 7 on the first hinges 311 and 312 or the second hinges 331 and 332.

In addition, a ring coupling portion 751 is formed on each of the first hinges 311 and 312 or each of the second hinges 331 and 332.

Meanwhile, in this embodiment, the drive module 7 is mounted on the second hinge 332 located on the right side as viewed from the first support 310 to the third support 330 in FIG. 2. Therefore, for convenience of explanation, the second hinge 332 located on the right side is hereinafter referred to as a right second hinge 332.

Here, a plurality of mounting protrusions 731 are formed on an inside of the ring member 730 at a predetermined interval along the circumferential direction of the ring member 730, and a ring coupling portion 751 to which the ring member 730 of the drive module 7 is coupled is provided circumferentially around an opening of the right second hinge 332. A plurality of catching portions 753 may be formed in the ring coupling portion 751 corresponding to the mounting protrusions 731.

Thus, when the drive module 7 is inserted into the right second hinge 332 and then the ring member 730 is rotated, the mounting protrusions 731 are rotated and caught by the catching portions 753, so that the drive module 7 is prevented from being released.

In addition, a catching lever 740 is provided on the body housing **710*a* to restrain rotation of the ring member 730 by being inserted into the ring member 730, so that after rotating the ring member 730, the catching lever 740 is pushed and inserted into the ring member 730 to thereby prevent rotation of the ring member 730**.

Meanwhile, as illustrated in FIG. 25, the right second hinge 332 according to the embodiment of the present disclosure may have a rotary shaft hole **3322*a* for receiving the drive shaft of the drive module 7. Here, the drive shaft 720 of the drive module 7 passes through the rotary shaft hole 3322*a* and is coupled to the right second hinge 332 when the drive module 7 is mounted on the right second hinge 332. Thus, when the drive shaft 720 is rotated in response to the driving of the drive module 7, the second support 320** is pivoted.

In more detail, in the embodiment of the present disclosure, as an example, as illustrated in FIG. 22, the second support 320 includes a shaft coupling bracket 3231 and a drive shaft fixing member 360.

The shaft coupling bracket 3231 may extend toward the drive shaft of the drive module 7. In the embodiment of the present disclosure, as an example, as illustrated in FIG. 21, the shaft coupling bracket 3231 extends from the second fixing plate 323 of the second support 320 toward the rotary shaft of the drive motor.

The drive shaft fixing member 360 fixes the drive shaft 720 inserted through the rotary shaft hole **3322*a* to the shaft coupling bracket 3231 when the drive module 7 is fastened to the right second hinge 332. Thus, when the drive shaft 720 is rotated in response to the driving of the drive module 7, the shaft coupling bracket 3231 is pivoted in response to the rotation of the drive shaft 720, so that the entire second support 320 is pivoted with respect to the third support 330**.

In the present disclosure, for example, the drive shaft 720 has a polygonal shape in cross-section. Although FIGS. 22 and 24 illustrate that the drive shaft 720 has a hexagonal shape in cross-section, the scope of the present disclosure is not limited thereto.

Corresponding to the cross-sectional shape of the drive shaft 720, as illustrated in FIG. 23, the drive shaft fixing member 360 according to the embodiment of the present disclosure may include a polygonal fixing hole 364 having a polygonal inner diameter. As described above, the polygonal fixing hole 364 may also be configured to have a hexagonal inner diameter corresponding to the drive shaft 720 having a hexagonal shape in cross-section.

This will be described in more detail with reference to FIG. 23. The drive shaft fixing member 360 may include a bracket fastening portion 361 and a pair of tightening members 362 and 363.

The bracket fastening portion 361 is provided at a first side of the drive shaft fixing member 360 with respect to the polygonal fixing hole 364, and is fastened to the shaft coupling bracket 3231 to fix the drive shaft fixing member 360 to the shaft coupling bracket 3231.

The pair of tightening members 362 and 363 are provided at a second side of the drive shaft fixing member 360 with respect to the polygonal fixing hole 364, and are spaced apart from each other with a space 365 formed therebetween. As illustrated in FIG. 22, the fixing hole 364 is formed between the pair of tightening members 362 and 363. In a state in which the drive shaft 720 is inserted into the polygonal fixing hole 364, the pair of tightening members 362 and 363 are approached to each other, so that the drive shaft 720 inserted into the polygonal fixing hole 364 is tightened and fixed.

In the embodiment illustrated in FIG. 23, as an example, the pair of tightening members 362 and 363 are branched from the bracket fastening portion 361, but the present disclosure is not limited thereto. For example, the pair of tightening members 362 and 363 may be configured such that two symmetrical members are combined at respective first sides thereof to form the bracket fastening portion 361, with respective second sides thereof spaced apart from each other.

In the embodiment of the present disclosure, as an example, the bracket fastening portion 361 is fastened to the shaft coupling bracket 3231 through bolt fastening. To this end, a plurality of bolt fastening holes 366*c* and 366*d* are formed in the bracket fastening portion 361, and in the present disclosure, as an example, the bolt fastening is performed in the biaxial direction. In other words, as an example, the plurality of bolt fastening holes 366*c* and 366*da* include a pair of bolt fastening holes 366*c* fastened to coupling holes 3231*a* formed in a plate surface of the shaft coupling bracket 3231, and a pair of bolt fastening holes 366*b* fastened to coupling holes 3234*a* formed in a pair of extension portions 3234 extending in a U-shape from the plate surface of the shaft coupling bracket 3231.

In addition, any one of the pair of tightening members 362 and 363 may have a first tightening hole 366*a* passing through a side thereof, and a remaining one of the pair of tightening members 362 and 363 may have a second tightening hole (not illustrated) for fastening a tightening bolt (not illustrated) passing through the first tightening hole so as to adjust the distance between the tightening members 362 and 363.

Meanwhile, the right second hinge 332 may include a first rotary part 3322 and a second rotary part 3321.

The first rotary part 3322 is rotated in conjunction with the right second support 320 in response to rotation of the drive shaft 720. In addition, the second rotary part 3321 is installed to be freely rotatable with respect to the first rotary part 3322, and is connected to the third support 330 to be rotated in conjunction with the third support 330. Here, as an example, the first rotary part 3322 and the second rotary part 3321 are coaxially coupled around the rotary shaft hole 3322*a*.

In the embodiment of the present disclosure, as an example, the first rotary part 3322 is axially coupled to the shaft coupling bracket 3231 to be rotated relative to the second rotary part 3321 in conjunction with rotation of the drive shaft 720.

FIG. 24 is a view illustrating a state in which the drive shaft fixing member 360 is removed, and FIG. 24 is a view illustrating a state in which the shaft coupling bracket 3231 is removed.

Referring to FIGS. 24 and 25, the shaft coupling bracket 3231 may further include a bracket coupling hole 3232 and a plurality of rotation synchronization holes 3233.

The bracket coupling hole 3322 is formed corresponding to the rotary shaft hole 3322*a*, and allows passage of the drive shaft 720 passing through the rotary shaft hole 3322*a*. The drive shaft 720 passing through the bracket coupling hole 3232 is fixed by the drive shaft fixing member 360.

The rotation synchronization holes 3233 are formed by passing through the plate surface of the shaft coupling bracket 3231 along the outer periphery of the bracket coupling hole 3232. Here, as illustrated in FIG. 25, the first rotary part 3322 may include a plurality of rotation synchronization protrusions 3322*b*. Thus, when the shaft coupling bracket 3231 is fastened to the first rotary part 3322, the rotation synchronization protrusions 3322*b* are inserted into the respective rotation synchronization holes 3233, so that when the drive shaft 720 is rotated in response to the driving of the drive module 7, the first rotary part 3322 is rotatable in conjunction with rotation of the shaft coupling bracket 3231.

The configuration of the right second hinge 332 driven by being coupled to the drive module 7 described with reference to FIGS. 22 to 25 is symmetrically implemented in the remaining second hinge 331. Similarly, the same mechanism may be applied to each of the first hinges 311 and 312, except that the first support 310 and the second support 320 are configured such that the first support 310 is pivoted in response to the driving of the drive module 7.

Hereinafter, a rotation restraining part 770 according to an embodiment of the present disclosure will be described in detail with reference to FIGS. 26 to 28.

As illustrated in FIGS. 2, 3, and 26, a hinge cover 780 may be installed where the drive module 7 is not installed from among the pair of first hinges 311 and 312 and the pair of second hinges 331 and 332. FIGS. 25 to 28 illustrate the first hinge 312 on the right side from among the first hinges 311 and 312.

The rotation restraining part 770 includes a rotary gear plate 776 rotated in conjunction with the first rotary part 3322, i.e., the first rotary part 3322 rotated in conjunction with the first support 310 or the second support 320, and a gear restraining member 771 installed on the second rotary part 3321.

The rotary gear plate 776 may have gear teeth circumferentially formed along an end thereof, and the gear restraining member 771 may have a gear insertion portion 772 formed at an end thereof to be insertable into a space between the gear teeth. Thus, when the gear insertion portion 772 is inserted into the space between the gear teeth of the rotary gear plate 776 by sliding the gear restraining member 771, rotation of the first rotary part 3322 is restrained.

Here, the rotation restraining part 770 may include a pair of restraining protrusions 774 protruding opposite to each other and being able to be elastically pressurized. In addition, a pair of restraining recesses 775 may be formed in a plate surface of the second rotary part 3321 at each side of the rotation restraining part 770 along the moving direction of the rotation restraining part 770 so that when the rotation restraining part 770 is moved in the vertical direction, the restraining protrusions 774 are inserted into the restraining recesses 775.

With this configuration, as illustrated in FIG. 2, when the drive module 7 is mounted on the second hinges 331 and 332, and the gear restraining member 771 and the rotary gear plate 776 of each of the pair of first hinges 311 and 312 are meshed with each other so that the pair of first hinges 311 and 312 are not rotated, the second support 320 performs a pivoting motion by a rotational force of the drive module 7, whereas the first support 310 is limited in pivoting motion, so that the user can exercise an elbow joint while a wrist joint is not moved.

In addition, when the drive module 7 is mounted on the first hinges 311 and 312, and the gear restraining member 771 and the rotary gear plate 776 of each the pair of second hinges 331 and 332 are meshed with each other so that the pair of second hinges 331 and 332 are not rotated, the first support 310 performs a pivoting motion by the rotational force of the drive module 7, whereas the second support 320 is limited in pivoting motion, so that the user can exercise the wrist joint while the elbow joint is not moved.

The above configuration may be applied equally to the second hinges 331 and 332.

FIG. 27 is a view illustrating the configuration of a rotation restraining part 770 according to another embodiment of the present disclosure.

In the embodiment illustrated in FIG. 28, a pair of restraining recesses 774*a* are formed on each side of the rotation restraining part 770, and a restraining rod 775*a* installed in the second rotary part 3321 is inserted into the restraining recesses 774*a*. Here, the restraining rod 775*a* is elastically pressurized in a direction of being inserted into the restraining recesses 774*a*, and, for example, may have a configuration that is pressurized in the direction of being inserted into the restraining recesses 774*a* by an elastic force of a spring.

Meanwhile, as illustrated in FIGS. 22 and 24, the drive module 7 according to the embodiment of the present disclosure may include a gear protrusion 750.

Here, the gear protrusion 750 is installed on a position capable of being in contact with the gear restraining member 771 at a position where the gear restraining member 771 is meshed with the rotary gear plate 776. Thus, the drive module 7 is prevented from being fastened to the first hinges 311 and 312 or the second hinges 331 or 332 in a state in which the gear restraining member 771 is meshed with the rotary gear plate 776, i.e., in a state in which the first rotary part 3322 and the second rotary part 3321 cannot be rotated relative to each other. In other words, this is because when fastening of the drive module 7 is allowed in a state in which the gear restraining member 771 is meshed with the rotary gear plate 776, the drive module 7 is rotated in a state in which rotation of the first rotary part 3322 is restrained, which may cause failure of the drive module 7.

Therefore, by not allowing fastening of the drive module 7 in a state in which rotation of the first rotary part 3322 is restrained, failure due to the above-described situation is prevented from occurring.

In addition, each of the first hinges 311 and 312 and the second hinges 331 and 332 may have a status display window 773 on which a current status is displayed in response to the operation of the gear restraining member 771. In other words, when the gear restraining member 771 is at a position meshed with the rotary gear plate 776, 'Lock' may be displayed on the status display window 773. On the other hand, when the meshing is released, 'Unlock' may be displayed on the status display window 773. On the other hand, this may be mechanically implemented so that such characters are displayed in conjunction with sliding movement of the gear restraining member 771.

In the above embodiment, as an example, the gear restraining member 771 is installed on the second rotary part 3321 and the rotary gear plate 776 is configured to be rotated in conjunction with the first rotary part 3322. However, the opposite example may be applied. In other words, the gear restraining member 771 may be installed on the first rotary part 3322, and the rotary gear plate 776 may be configured to be rotated in conjunction with the second rotary part 3321.

Meanwhile, the rehabilitation exercise apparatus 1 according to an embodiment of the present disclosure may enable the user to perform rehabilitation by selectively mounting the drive module 7 to each hinge in response to a position of the upper or lower limb to be exercised.

For example, when the drive module 7 is mounted on the left first hinge 311 or the left second hinge 331, the rehabilitation exercise device 1 according to the embodiment of the present disclosure is worn on a right upper limb to exercise, without causing interference of the drive module 7 with a user's torso. In this case, when the drive module 7 is mounted on the left first hinge 311, exercise of a right wrist joint is possible. On the other hand, when the drive module 7 is mounted on the left second hinge 331, exercise of a right elbow joint is possible.

When the drive module 7 is mounted on the right first hinge 312 or the left second hinge 332, the rehabilitation exercise device 1 according to the embodiment of the present disclosure is worn on a left upper limb to exercise, without causing interference of the drive module 7 with the user's torso. In this case, when the drive module 7 is mounted on the right first hinge 312, exercise of a left wrist joint is possible. On the other hand, when the drive module 7 is mounted on the right second hinge 332, exercise of a left elbow joint is possible.

Meanwhile, the rehabilitation exercise device 1 comprises at least one type of sensors S1, S2 for detecting a first information. The information processing terminal 4 according to the embodiment of the present invention can transmit a second information to the rehabilitation exercise device 1 via a wireless communication network 6.

Here, a rehabilitation exercise load is controlled based on the first information detected by the sensors S1, S2 and the second information transmitted from the information processing terminal 4.

FIG. 29 is a view illustrating control block diagrams for the rehabilitation exercise device 1 and the information processing terminal 4 according to the embodiment of the present disclosure.

Referring to FIG. 29, the rehabilitation exercise device 1 may further comprise the drive motor 91 described above, a device communication unit 92, at least one type of sensors S1, S2 and a device controller 93.

The device communication unit 92 communicate with the information processing terminal 4 via a wireless communication network 6 as described above. As described above, the device communication unit 92 may communicate with the information processing terminal 4 via a Wi-Fi network or a Bluetooth network.

The device controller 93 controls the drive motor 91 to control the rehabilitation exercise load based on the first information detected by the sensors S1, S2 and the second information received from the information processing terminal 4 by the device communication unit 92.

The information processing terminal 4 according to the embodiment of the present invention may comprise a terminal communication unit 41, a rehabilitation management application 42, an image display 44, a user input unit 45 and a terminal controller 43.

The terminal communication unit 41 can be connected to the device communication unit 92 of the rehabilitation exercise device 1 via a wireless communication network 6. Here, the terminal communication unit 41 can also communicate with the rehabilitation exercise device 1 via a Wi-Fi network or a Bluetooth network.

The image display unit 44 displays an image on a screen by means of the display panel such as an LCD panel or an OLED panel. In the present invention, a graphic user interface provided by the rehabilitation management application 42 can be displayed by means of the image display unit 44.

The user input unit 45 converts an input of a user operation into the input signal and then transmits the signal to the terminal controller 43. The user input unit 45 can be configured in various types according to a type of the information processing terminal 4 of the embodiment of the present invention.

The device controller 93 performs main functions of the information processing terminal 4 such as calculation, command processing, etc. The device controller 93 may comprise hardwares such as a processor, e.g., CPU or AP, a memory, a storage unit, a graphic processor, etc. and softwares such as an operating system.

The rehabilitation management application 42 is installed on the information processing terminal 4 and then is executed such that it manages generally the rehabilitation exercise using the rehabilitation exercise device 1 according to the embodiment of the present invention. Herein, the term "application" is used and can be also called application program, software, etc.

User uses the rehabilitation management application 42 to perform various functions provided by the rehabilitation management application 42. For example, the rehabilitation management application can set a torque of the drive motor 91 and can receive the history of the rehabilitation exercise from the rehabilitation exercise device 1 and store it.

Also, the rehabilitation management application connects its information processing terminal 4 to a terminal of the manager such as a hospital or a server via a communication network to transmit the rehabilitation exercise history to a doctor or a rehabilitation exercise therapist for the management of the rehabilitation exercise. Besides, other various functions can be provided by the rehabilitation management application 42 according to the present invention.

Meanwhile, as an example, sensors S1, S2 of the rehabilitation exercise device 1 according to the embodiment of the present invention comprises a mounting position detecting part S1 and an angle sensor S2.

As described above, the rehabilitation exercise unit 3 is located on the holder 5 and is supported by the holder 5 such that it can move between a position on which the rehabilitation exercise unit rests as shown in FIG. 2 and a position where the rehabilitation exercise unit 3 is elevated at a predetermined angle as shown in FIG. 3. Hereinafter, the position of the rehabilitation exercise unit 3 as shown in FIG. 2 is referred to as the first position and the position of the rehabilitation exercise unit 3 as shown in FIG. 3 is referred to as the second position.

Here, the angle sensor S2 according to the embodiment of the present invention can detect an angle of the rehabilitation exercise device 1 with respect to the gravity direction according to a supporting state of the holder 5. In the embodiment of the present invention, as an example, the angle sensor S2 is a Gyro sensor S1, S2 which detects an angle change in a gravity direction or a IMU sensor S2, S2 such as an acceleration sensor S1, S2.

The mounting position detecting part S1 detects a location where the drive module 7 is installed on either a pair of the first hinges 311, 312 or a pair of the second hinges 331, 332.

The mounting position detecting part S1 transmits information of the detected mounting position to the device controller 93. Here, examples of the mounting position detecting part S1 will be described below.

Meanwhile, the device controller 93 controls the drive motor 91 based on the first information and the second information such that when the device is operated on an active exercise mode of the rehabilitation exercise, the torque applied to a pair of the first hinges 311, 312 or a pair of the second hinges 331, 332 is compensated, for the rehabilitation exercise in the active exercise mode.

When the user uses the rehabilitation unit 3 according to the embodiment of the present invention for the active exercise, it is advisable that the load experienced by the user is controlled to become zero. However, the generated load depends on weight and length of the rehabilitation exercise unit 3 and weight and length of user's arms and legs.

Also, since the rehabilitation exercise unit 3 according to the embodiment of the present invention is displaced between the first position and the second position, the effect of gravity varies depending on each position.

FIG. 30 describes elements which affect a rehabilitation exercise load in the rehabilitation exercise system for upper and lower limbs according to the embodiment of the present invention. FIG. 30 (*a*) describes a state that the second hinges 331, 332 are rotated when the rehabilitation exercise unit 3 is located at the first position and FIG. 30 (*b*) describes a state that the second hinges 331, 332 are rotated when the rehabilitation exercise unit 3 is located at the second position.

Torque $\tau$ at the second hinges 331, 332 varies since the effect of gravity g varies according to the weight m and the length l to the center of weight. The total torque $\tau_{total}$ applied to the second hinges 331, 332 is represent as [formula 1] as follows.

$$\tau_{total}=\tau_m-\tau_f(\dot{\theta})-m_h g l_h \cos\theta-m_d g l_d \cos\theta \quad \text{[formula 1]}$$

In [formula 1], $\tau_m$ represents an output torque of the drive motor 91 controlled by the device controller 93 and $\tau_f(\dot{\theta})$ represents a friction force torque caused by a friction force generated when the first hinges 311, 312 and the second hinges 331, 332 rotate.

And, $m_h$ represents a user weight corresponding to a weight of user's upper and lower limbs applied to the rehabilitation exercise unit 3 and $l_h$ presents a user distance which is a distance from a rotation axis O of the drive motor 91 to a weight center corresponding to a user's weight. Also, $m_d$ represents a device weight of the rehabilitation exercise unit 3, and $l_d$ represents a device distance value which is a distance from a rotation axis O of the drive motor 91 to a weight center corresponding to a device weight, and $\theta$ represents a control rotation angle of the drive motor 91.

Here, since the total torque $\tau_{total}$ should be zero for the active exercise, [formula 1] is represented as [formula 2].

$$\tau_m=\tau_f(\dot{\theta})-m_h g l_h \cos\theta+m_d g l_d \cos\theta \quad \text{[formula 2]}$$

In [formula 2], since $\tau_f(\dot{\theta})$ can be registered in advance by experiments, it is a constant and a device weight $m_d$ is also a constant.

And, regarding the control rotation angle of the drive motor 91, a rotation direction is changed according to the mounting position of the drive module 7 and which side of the left and right sides the drive module is mounted at a pair of the first hinges 311, 312 or a pair of the second hinges 331, 332 and, an initial offset is changed according to the elevation angle of the rehabilitation exercise unit 3 as described above.

Accordingly, based on the detection of the mounting position detecting part S1 and the detection of the angle sensor S2, the control rotation angle $\theta$ of the drive motor 91 is calculated by [formula 3] as follows.

$$\theta=\alpha\theta_{motor}+\theta_{offset} \quad \text{[formula 3]}$$

In [formula 3], $\alpha$ represents a rotation direction of the motor set according to the mounting position information detected by the mounting position detecting part S1 and is set as 1 or −1 based on the left side or the right side at a pair of the first hinges 311, 312 or a pair of the second hinges 331, 332.

And, $\theta_{motor}$ is an absolute rotation angle of the drive motor 91 and $\theta_{offset}$ is a gravity direction angle corresponding to the elevation angle of the rehabilitation exercise unit 3 detected by the angle sensor S2.

In [formula 2], the user weight and the user distance vary according to the user who performs the rehabilitation exercise using the rehabilitation exercise unit 3 according to the embodiment of the present invention, and the user weight and the user distance can be input by the user or the rehabilitation manager using the information processing terminal 4, and corresponding information can be transferred as the second information from the information processing terminal 4 to the rehabilitation exercise device.

As described above, in the embodiment of the present invention, since the length of the second support 320 can vary, the distance $l_d$ is also changed. Accordingly, the device distance is detected as the first information by the installation of another sensor which detects the length change of the second support 320 or is input into the information processing terminal 4 by a user or a rehabilitation manager so as to be provided as the second information.

According to the above, the device controller 93 of the rehabilitation exercise unit 3 according to the embodiment of the present invention can control the drive motor 91 based on the first information and the second information such that the rehabilitation exercise load experienced by the user when the user exercises in the active exercise mode, i.e., the total torque $\tau_{total}$ becomes 'zero'.

Hereinafter, referring to FIG. 31 and FIG. 32, examples of the mounting position detecting part S2 according to the embodiment of the present invention will be described.

The mounting position detecting part S1 detects the mounting position where the drive module 7 is mounted from among the pair of first hinges 311 and 312 and the pair of second hinges 331 and 332. In the embodiment of the present disclosure, as an example, the mounting position detecting part S1 includes a to-be-detected module M,810*a*, 810*b*, 810*c*, and 810*d*, and a sensor module HS.

The to-be-detected module M,810*a*, 810*b*, 810*c*, and 810*d* is installed on each of the pair of first hinges 311 and 312 and the pair of second hinges 331 and 332. In addition, the sensor module HS is installed in the drive module 7, and recognizes the to-be-detected module M,810*a*, 810*b*, 810*c*, and 810*d* when the drive module 7 is mounted on any one of the first hinges 311 and 312 and the second hinges 331 and 332.

Here, the respective to-be-detected modules M,810*a*, 810*b*, 810*c*, and 810*d* installed on the first hinges 311 and 312 and the second hinges 331 and 332 are configured to be distinguishably recognized, so that the sensor module HS recognizes where the drive module 7 is installed from among the first hinges 311 and 312 and the second hinges 331 and 332.

FIGS. 31 and 32 are views illustrating an example of the configuration of a mounting position detecting part S1 according to an embodiment of the present disclosure. As an example, the sensor module HS according to the embodiment of the present disclosure includes a Hall sensor.

As an example, as illustrated in FIG. 22, the Hall sensor is installed in the body housing 710 of the drive module 7.

As an example, the respective to-be-detected modules M,810*a*, 810*b*, 810*c*, and 810*d* include magnet members M and magnet holes 810*a*, 810*b*, 810*c*, and 810*d*. The respective magnet members M may be embedded in the first hinges 331 and the second hinges 331 and 332 at positions corresponding to each other. Here, the magnet members M are installed at positions detectable by the Hall sensor when the drive module 7 is mounted on the first hinges 311 and 312 or the second hinges 331 and 332.

As illustrated in FIG. 31, the magnet holes 810*a*, 810*b*, 810*c*, and 810*d* are formed in the first hinges 311 and 312 and the second hinges 331 and 332, respectively, to allow exposure of the magnet members M therethrough. Here, the respective magnet holes 810*a*, 810*b*, 810*c*, and 810*d* may be configured to differ in at least one of position and size, so that when detecting the magnetic fields of the magnet members M, the Hall sensor recognizes the mounting position of the drive module 7 by detecting magnetic fields having different characteristics according to the positions and sizes of the magnet holes 810*a*, 810*b*, 810*c*, and 810*d*.

Referring to FIG. 32, the four magnet holes 810*a*, 810*b*, 810*c*, and 810*d* formed in the first hinges 311 and 312 and the second hinges 331 and 332, respectively, may be located at upper and lower positions with respect to the Hall sensor. For example, when the magnet hole 810*a* is formed in the right first hinge 312, the magnet hole 810*b* is formed in the left first hinge 311, the magnet hole 810*c* is formed in the right second hinge 332, and the magnet hole 810*d* is formed in the left second hinge 331, during mounting of the drive module 7, the mounting position of the drive module 7 is recognized by detecting magnetic fields having different characteristics according to the positions of the magnet holes 810*a*, 810*b*, 810*c*, and 810*d*.

Although in FIG. 32 it is illustrated that the magnet holes 810*a*, 810*b*, 810*c*, and 810*d* have different positions and sizes, other configurations are possible as long as magnetic field characteristics are distinguishable.

In another embodiment, the to-be-detected module M,810*a*, 810*b*, 810*c*, and 810*d* may include a short-range communication tag, for example, a RF or NFC tag, in which information on a corresponding position is embedded, and the sensor module HS may include a reader that recognizes the information embedded in the tag.

Although exemplary embodiments of the present disclosure have been described with reference to the accompanying drawings, those skilled in the art will appreciate that various modifications, additions and substitutions are possible, without departing from the scope and spirit of the disclosure as defined in the appended claims. Thus, the above-described exemplary embodiments are intended to be illustrative in all respects, rather than restrictive, of the present disclosure.

The present disclosure can find application in a rehabilitation exercise device for rehabilitation of a patient's upper or lower limb.

What is claimed is:

1. A rehabilitation exercise system for upper and lower limbs, comprising: a rehabilitation exercise device for rehabilitation of arms or legs, and an information processing terminal which is connected to the rehabilitation exercise device via a wireless communication network;

wherein the rehabilitation exercise device comprises at least one sensor which detect a first information;

wherein the information processing terminal is configured to transmit a second information to the rehabilitation exercise device via the wireless communication network;

wherein the rehabilitation exercise device is configured to control a rehabilitation exercise load based on the first information and the second information, wherein the rehabilitation exercise device comprises:

a rehabilitation exercise unit, and a holder on which the rehabilitation exercise unit is located and configured to support the rehabilitation exercise unit so as to move between a first position on which the rehabilitation exercise unit rests and a second position where the rehabilitation exercise unit is elevated at a predetermined angle;

wherein the at least one sensor comprise an angle sensor which detects an angle of the rehabilitation exercise device with respect to a gravity direction according to a state of being supported by the holder;

wherein the rehabilitation exercise unit comprises:

a first support for supporting a hand or a foot, a second support for supporting a forearm of the upper limb or a calf of the lower limb, a pair of first hinges for rotatably connecting the first support and the second support, a third support for supporting an upper arm of the upper limb or a thigh of the lower limb, a pair of second hinges for rotatably connecting the second support and the third support, a drive module configured to be selectively mounted on any one of the pair of first hinges and the pair of second hinges, a drive motor which pivots the first support or the second support being embedded in the drive module, and a device controller for controlling a torque of the drive motor based on the first information and the second information to control a rehabilitation exercise load;

wherein the at least one sensor further comprises a mounting position detecting part which detects a location where the drive module is mounted on the pair of first hinges or the pair of second hinges.

2. The rehabilitation exercise system according to claim 1, wherein during the operation in an active mode, the device controller is configured to control the drive motor based on the first information and the second information so as to compensate a torque applied to the pair of first hinges or the pair of second hinges for the rehabilitation in the active mode.

3. The rehabilitation exercise system according to claim 2, wherein the first information comprises a mounting position information of the drive module detected by the mounting position detecting part and a gravity direction angle detected by the angle sensor;

wherein the second information comprises:

a user's weight corresponding to a weight of the upper limb or the lower limb applied to the rehabilitation exercise unit; and a user's distance which is a distance from a rotation axis of the drive motor to a weight center corresponding to the user's weight.

4. The rehabilitation exercise system according to claim 3, wherein during the operation in the active mode, the device controller is configured to control the drive motor based on the following formula:

$$\tau_m=\tau_f(\dot{\theta})+m_h g l_h \cos\theta+m_d g l_d \cos\theta)$$

where $\tau_m$ represents a output torque of the drive motor controlled by the device controller, $\tau_f(\dot{\theta})$ is a pre-registered constant which represents a friction force torque caused by a friction force generated when the first hinges and the second hinges pivot, $m_h$ represents the user's weight, $l_h$ represents the user's distance, $m_d$ is a pre-registered constant which represents a device weight of the rehabilitation exercise unit, $l_d$ represents a device distance value which is a distance from a rotation axis of the drive motor to a weight center corresponding to the device weight, and $\theta$ represents a control rotation angle of the drive motor;

wherein $\theta$ is determined by the following formula:

$$\theta=\alpha\theta_{motor}+\theta_{offset},$$

where $\alpha$ represents a rotation direction value of the motor set according to the mounting position information and is set as 1 or −1 based on a left side or a right side at the pair of the first hinges or the pair of the second hinges, $\theta_{motor}$ is an absolute rotation angle of the drive motor, and $\theta_{offset}$ is the gravity direction angle.

5. The rehabilitation exercise system according to claim 4, wherein the second support has adjustable length;

wherein a device distance according to the length adjustment of the second support is measured and registered as the first information, or is transmitted from the information processing terminal to the rehabilitation exercise device and registered as the second information.

6. The rehabilitation exercise system according to claim 2, wherein the mounting position detecting part comprises:

a to-be-detected module configured to be installed on each of the pair of first hinges and the pair of second hinges; and a sensor module installed on the drive module and configured to recognize the to-be-detected module when the drive module is mounted on any of the pair of first hinges and the pair of second hinges;

wherein the to-be-detected module installed on each of the pair of first hinges and the pair of second hinges is configured to be distinguishably recognized.

7. The rehabilitation exercise system according to claim 6, wherein the sensor module comprises a Hall sensor;

wherein each of the to-be-detected module comprises magnet members embedded in each of the pair of first hinges and the pair of second hinges at positions corresponding to each other; and a magnet hole formed in each of the pair of first hinges and the pair of second hinges to allow exposure of the magnet members to outside;

wherein each magnet hole is configured to differ in at least one of a position and a size so that the mounting position is distinguishably recognized by the Hall sensor.

8. The rehabilitation exercise system according to claim 6, wherein the to-be-detected module is installed on each of the pair of first hinges and the pair of second hinges and comprises a short-range communication tag in which information about a corresponding position is embedded;

wherein the sensor module comprises a reader which recognizes information stored in the tag when the drive module is mounted on each of the pair of first hinges and the pair of second hinges.

* * * * *